(12) United States Patent
DiGianfilippo et al.

(10) Patent No.: US 6,199,603 B1
(45) Date of Patent: Mar. 13, 2001

(54) COMPOUNDING ASSEMBLY FOR NUTRITIONAL FLUIDS

(75) Inventors: Aleandro DiGianfilippo, Scottsdale, AZ (US); James R. Hitchcock, Barrington, IL (US); Richard S. Pierce, Glendale, AZ (US)

(73) Assignee: Baxter International Inc., Deerfield, IL (US)

(*) Notice: Subject to any disclaimer, the term of this patent is extended or adjusted under 35 U.S.C. 154(b) by 0 days.

(21) Appl. No.: 09/372,284

(22) Filed: Aug. 11, 1999

Related U.S. Application Data

(60) Provisional application No. 60/096,496, filed on Aug. 14, 1998.

(51) Int. Cl.[7] ................................ B65B 1/30; B65B 3/26
(52) U.S. Cl. ......................... 141/83; 141/94; 141/100; 141/104; 222/52; 73/61.43; 73/61.44; 73/61.61
(58) Field of Search ................................... 141/9, 83, 94, 141/100, 104; 222/52; 73/61.43, 61.44, 61.61

(56) References Cited

U.S. PATENT DOCUMENTS

| | | | |
|---|---|---|---|
| 3,155,898 | 11/1964 | Chope | 324/58.5 |
| 3,233,173 | 2/1966 | Lees et al. | 324/61 |
| 3,643,507 | 2/1972 | Garrett | 73/194 R |
| 3,774,238 | 11/1973 | Hardway, Jr. | 324/61 |
| 4,074,184 | 2/1978 | Dechene et al. | 324/30 |
| 4,227,151 | 10/1980 | Ellis et al. | 324/448 |
| 4,266,188 | 5/1981 | Thompson | 324/65 |
| 4,410,981 | 10/1983 | Flory | 370/109 |
| 4,467,844 | 8/1984 | Di Gianfilippo et al. | 141/1 |
| 4,475,666 | 10/1984 | Bilbrey et al. | 222/14 |
| 4,484,135 | 11/1984 | Ishihara et al. | 324/71.1 |
| 4,513,796 | 4/1985 | Miller et al. | 141/83 |
| 4,590,431 | 5/1986 | Anderson et al. | 324/443 |

(List continued on next page.)

FOREIGN PATENT DOCUMENTS 0721103   7/1996   (EP).

*Primary Examiner*—Timothy L. Maust
(74) *Attorney, Agent, or Firm*—Jeffrey C. Nichols; Mark J. Buonaiuto; Francis C. Kowalik

(57) ABSTRACT

A mixing assembly which transfers a number of nutritional fluids from individual source containers into a collection container while noninvasively sensing the type of fluid being transferred is provided. The mixing assembly utilizes a transfer set to establish fluid communication between the source containers and the collection container. A sensing assembly is configured to noninvasively sense a number of the types of fluid flowing through the transfer set to help to prevent improper mixing. For other fluids for which the sensing assembly alone may not be able to distinguish with the desired accuracy, the mixing device utilizes a method to approximate the flow rate of that fluid with the flow rate also providing an indication of that type of fluid. By combining the output of the sensing assembly with the flow rate determination, additional fluids can be identified.

The assembly includes a controller that executes a number of routines that minimize the occurrence of false alarms, while insuring accurate and reliable compounding of prescriptions.

23 Claims, 30 Drawing Sheets

U.S. PATENT DOCUMENTS

| | | | |
|---|---|---|---|
| 4,648,430 | 3/1987 | DiGianfilippo et al. | 141/1 |
| 4,653,010 | 3/1987 | Figler et al. | 364/502 |
| 4,696,671 | 9/1987 | Epstein et al. | 604/67 |
| 4,712,590 | 12/1987 | DiGianfilippo | 141/83 |
| 4,745,953 | 5/1988 | Kobayashi et al. | 141/1 |
| 4,751,476 | 6/1988 | Meijer | 331/65 |
| 4,769,001 | 9/1988 | Prince | 604/4 |
| 4,807,676 | 2/1989 | Cerny et al. | 141/98 |
| 4,838,323 | 6/1989 | Watts | 141/1 |
| 4,896,099 | 1/1990 | Suzuki | 324/667 |
| 4,899,101 | 2/1990 | Porges | 324/663 |
| 4,924,702 | 5/1990 | Park | 73/304 |
| 4,925,444 | 5/1990 | Orkin et al. | 604/80 |
| 4,928,065 | 5/1990 | Lane et al. | 324/464 |
| 4,935,207 | 6/1990 | Stanbro et al. | 422/68.1 |
| 5,033,644 | 7/1991 | Tentler | 222/57 |
| 5,040,699 | 8/1991 | Gangemi | 222/1 |
| 5,056,568 | 10/1991 | DiGianfilippo et al. | 141/1 |
| 5,068,617 | 11/1991 | Reich | 324/663 |
| 5,187,444 | 2/1993 | Kumada et al. | 324/663 |
| 5,208,544 | 5/1993 | McBrearty et al. | 324/687 |
| 5,209,275 | 5/1993 | Akiba et al. | 141/83 |
| 5,213,142 | 5/1993 | Koch et al. | 141/59 |
| 5,239,860 | 8/1993 | Harris et al. | 73/61.48 |
| 5,255,656 | 10/1993 | Rader et al. | 123/494 |
| 5,260,665 | 11/1993 | Goldberg et al. | 324/636 |
| 5,266,899 | 11/1993 | Bull et al. | 324/439 |
| 5,289,132 | 2/1994 | Oksman et al. | 324/444 |
| 5,296,843 | 3/1994 | Wohlstein et al. | 340/603 |
| 5,304,126 | 4/1994 | Epstein et al. | 604/67 |
| 5,317,506 | 5/1994 | Coutre et al. | 364/413.02 |
| 5,373,244 | 12/1994 | Marrelli | 324/640 |
| 5,404,920 | 4/1995 | Custer | 141/83 |
| 5,464,392 | 11/1995 | Epstein et al. | 604/67 |
| 5,496,273 | 3/1996 | Pastrone et al. | 604/67 |
| 5,503,624 | 4/1996 | Roeher et al. | 604/65 |
| 5,507,412 | 4/1996 | Ebert et al. | 222/63 |
| 5,510,621 | 4/1996 | Goldman | 250/343 |
| 5,522,798 | 6/1996 | Johnson et al. | 604/65 |
| 5,609,576 | 3/1997 | Voss et al. | 604/67 |
| 5,612,622 | 3/1997 | Goldman et al. | 324/444 |
| 5,616,124 | 4/1997 | Hague et al. | 604/65 |
| 5,630,799 | 5/1997 | Beiser | 604/66 |
| 5,645,531 | 7/1997 | Thompson et al. | 604/67 |
| 5,653,681 | 8/1997 | Ellingboe | 604/4 |
| 5,927,349 | 7/1999 | Martucci et al. | 141/83 |

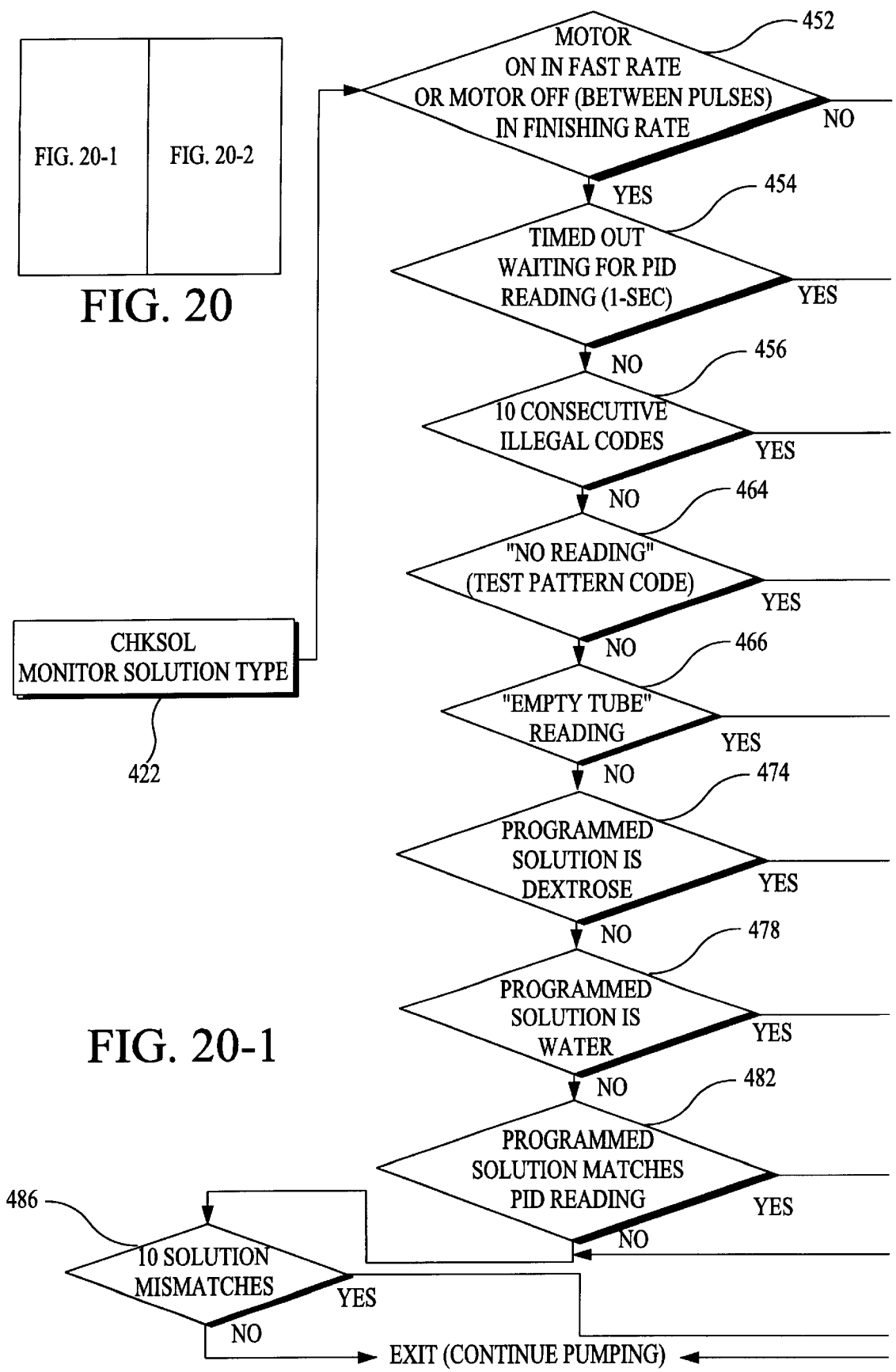

COMPOUNDING ASSEMBLY FOR NUTRITIONAL FLUIDS

This application claims the benefit of U.S. Provisional Application No. 60/096,496, filed Aug. 14, 1998.

BACKGROUND OF THE INVENTION

The present invention relates to assemblies for transferring a plurality of individual fluids from multiple source containers into a collecting container, and specifically relates to such an assembly which controllably transfers the individual fluids to a collecting container in at least partial dependence on a determination of the type of the transferred fluids.

In many instances, an individual must be fed by administration of a nutritional solution to that patient. For example, such feeding may be accomplished by administration of a nutritional solution directly to a patent's digestive system or by administration of a solution into a patients intravenous system. Frequently, the desired solution to be administered will vary between individuals, and in many settings, such as hospitals or other care giving facilities, there may be a sizable number of individuals needing such solutions. Therefore, it is desirable that these solutions are prepared in a safe, efficient and accurate manner.

There are several devices which are designed to compound a desired nutritional solution in a collection container by varying the amount of each of a number of nutritional components which are added to the container. One such exemplary device is the Automix® compounder sold by Baxter Healthcare Corporation of Deerfield, Ill.

In one method of utilizing such devices, a pharmacist or nutritional caregiver will determine the nutritional solution which is to be administered and specify the desired quantity of each of the nutritional components which are needed to form the desired solution. This information will then be utilized to compound the desired solution. A number of source containers of the various individual nutritional components may be clustered about and connected to the collection container for the nutritional solution. A desired quantity of one or more of the components is then transferred from the source containers to the collection container in a controlled manner. Upon completion the collection container is disconnected and eventually transported to the individual for administration.

As can be appreciated, it is highly desirable that the compounding method add the nutritional components to the collection container in an accurate manner. In one example, the method may utilize a compounder which transfers, in a controlled manner, the desired quantities of the nutritional components to the collection container. Although the compounder may be properly instructed to make the nutritional solution, an accurate determination of the quantity and the type of component being added to the container during the transferring process is also desirable.

To promote sterility of the nutritional solution, surfaces which come into contact with any of the nutritional fluids must be kept clean. To implement this requirement, compounding devices frequently utilize a sterile disposable apparatus or transfer set for connecting the containers housing the sterile nutritional components to the collection container. At appropriate times, the transfer set will be replaced, with the replaced set properly disposed of.

These transfer sets, however, may make it difficult to use fluid sensors which must contact a fluid to distinguish the different types of fluids in the compounding method. Thus, typically if transfer sets are used, it is highly desirable that the compounding apparatus be operable without utilizing sensors which require contact with the fluid to function properly.

Generally, in compounding solutions such as nutritional solutions, the type of source solution in a particular container is one of the inputs to the compounder. However, in some instances, there may be a possibility that the type of solution is input incorrectly. It would be highly desirable to have a compounder that independently verifies the type of solution which flows from a particular container so that any errors may be detected.

One type of sensing system which may find use in compounding methods is disclosed in published U.S. Pat. No. 5,612,622, issued Mar. 18, 1997 entitled "APPARATUS FOR IDENTIFYING CONTAINER COMPONENTS USING ELECTRICAL CONDUCTIVITY". However, it has been found that with such a system distinguishing between two or more of the fluids which are typically used in nutritional compounding methods may be difficult. Thus other types of sensing systems or processes may be desirable.

It is therefore an object of the present invention to provide an assembly for transferring component fluids from a plurality of individual source containers to a receiving or collection container. A related object is to provide such an assembly which controllably transfers desired volumes of the component fluids and compounds a desired nutritional solution in a collection container in at least partial dependence on a determination of the type of the fluids being transferred.

Another object of the present invention is to provide an assembly for individually transferring and compounding a number of predetermined nutritional solutions in a collection container in an efficient and accurate manner.

A further object of the present invention is to provide an assembly for transferring a plurality of component fluids and compounding a desired solution by adding in a controlled manner the components to a collection container to form the desired solution. A related object is to provide as an input to such a compounding process, the type and amount of components which have been transferred to the collection container.

Yet another object of the present invention is to provide an assembly for transferring component fluids with the assembly adapted to utilize a disposable transfer set to connect source component containers to a receiving or collection container. A related object is to provide such an assembly having sensors uniquely suited to operate with such a set and without requiring contact with fluids during the compounding process.

A still further object of the present invention is to provide an assembly for transferring component fluids and compounding a desired solution, with the assembly having the ability to check the type of component fluid being transferred during the compounding process. A related object is to provide such an assembly where the types of component fluids being transferred are input into the system and the compounding assembly independently checks the type of component solutions during the compounding process.

Still another object of the present invention is to provide such an improved assembly for transferring component fluids and compounding a desired solution, with the assembly having a controller that utilizes software routines that carry out compounding processes in a way which minimizes the probability of false alarm signals and yet achieves safe and reliable operation.

Yet another object of the present invention is to provide such an assembly which is adapted to provide the necessary alarm signal indications when such are warranted during operation, but which utilizes operating strategies which preclude alarms when it is known from actual sensed conditions that some further limited compounding activity, for example, can safely proceed.

Still another object of the present invention is to provide such an improved assembly which has sophisticated operation in that it can distinguish between the absence of a transfer set conduit, the presence of such a conduit and when it is empty, and can identify the fluid within the conduit in a noninvasive manner, and use such distinguishing capabilities to control the producing of selective alarm indications in a very accurate manner.

A more detailed object lies in the provision of controlling the pump motors associated with each of a plurality of source containers in a transfer set in a manner whereby it is extremely improbable that a motor can be inadvertently caused to run as a result of a single switch failure.

Another object of the present invention is to provide such an improved assembly which advantageously utilizes the capability of identifying fluid within a transfer set conduit and utilize such knowledge together with flow rate information during a compounding operation to safely and reliably complete a compounding operation under closely monitored and known conditions that would otherwise trigger a preselected alarm indication condition. A related object lies in the provision of providing an improved assembly that is convenient for a user to operate and which minimizes the generation of unwanted and disruptive false alarm indications during operation.

SUMMARY OF THE INVENTION

The present invention provides an assembly which controllably transfers component fluids from a plurality of individual source containers through a transfer set to form or compound a desired mixture in a collection container while determining or sensing the type of fluid being transferred. The identified component fluid type may then be compared with the desired fluid type to verify that the fluid being transferred matches the desired fluid. To this end, the transferring assembly of the present invention includes a sensing assembly which is in sensory contact with the component fluid as the fluid flows through the transfer set and provides a distinguishing characteristic of the solution being transferred. In an embodiment, the sensing assembly is in noninvasive sensory contact with the component fluid during flow. The distinguishing characteristic provided by the sensing assembly accurately identifies at least one of the component fluids without the necessity of further input. In a further embodiment, the transferring assembly identifies a distinguishing characteristic which may correspond to a plurality of fluid types. Then, if the distinguishing characteristic is insufficient to identify the particular fluid, the transferring assembly examines an additional input characteristic of at least one of the component solution types and identifies the component fluid with the desired accuracy.

In an embodiment, the mixing assembly includes a pump operatively acting on at least one of the component fluids within the transfer set to force a flow of that fluid along at least a portion of the transfer set. The rate of the flow particularly within the transfer set, varies in at least partial dependence on a distinguishing characteristic of the fluid. The mixing assembly further includes the ability to determine the differences between the flow rates of the component fluids thereby providing a further distinguishing characteristic of the component fluid flowing through the transfer set.

In an embodiment, the sensing assembly includes a plurality of sensors which are disposed in close proximity to tubing forming a part of the transfer set. A signal transmitted by one of the sensors is received by a second sensor, and the received signal is indicative of a distinguishing characteristic of the fluid within the tubing.

In an embodiment, the mixing assembly includes a weight sensor operatively contacting a collection container to distinguish between varying flow rates of different component solution by measuring weight change of the container over a predetermined time interval.

In the embodiments described, the mixing assembly includes control means that is adapted to control the operation of the assembly, acquire, receive and process the signals that are generated by various sensors of the assembly and control the operation of the pump motors and selectively generate preselected alarm indication signals during operation of the assembly and includes an alarm means which provides both visual and audio alarm indications to the user.

DESCRIPTION OF THE PREFERRED EMBODIMENT

Figure 1:
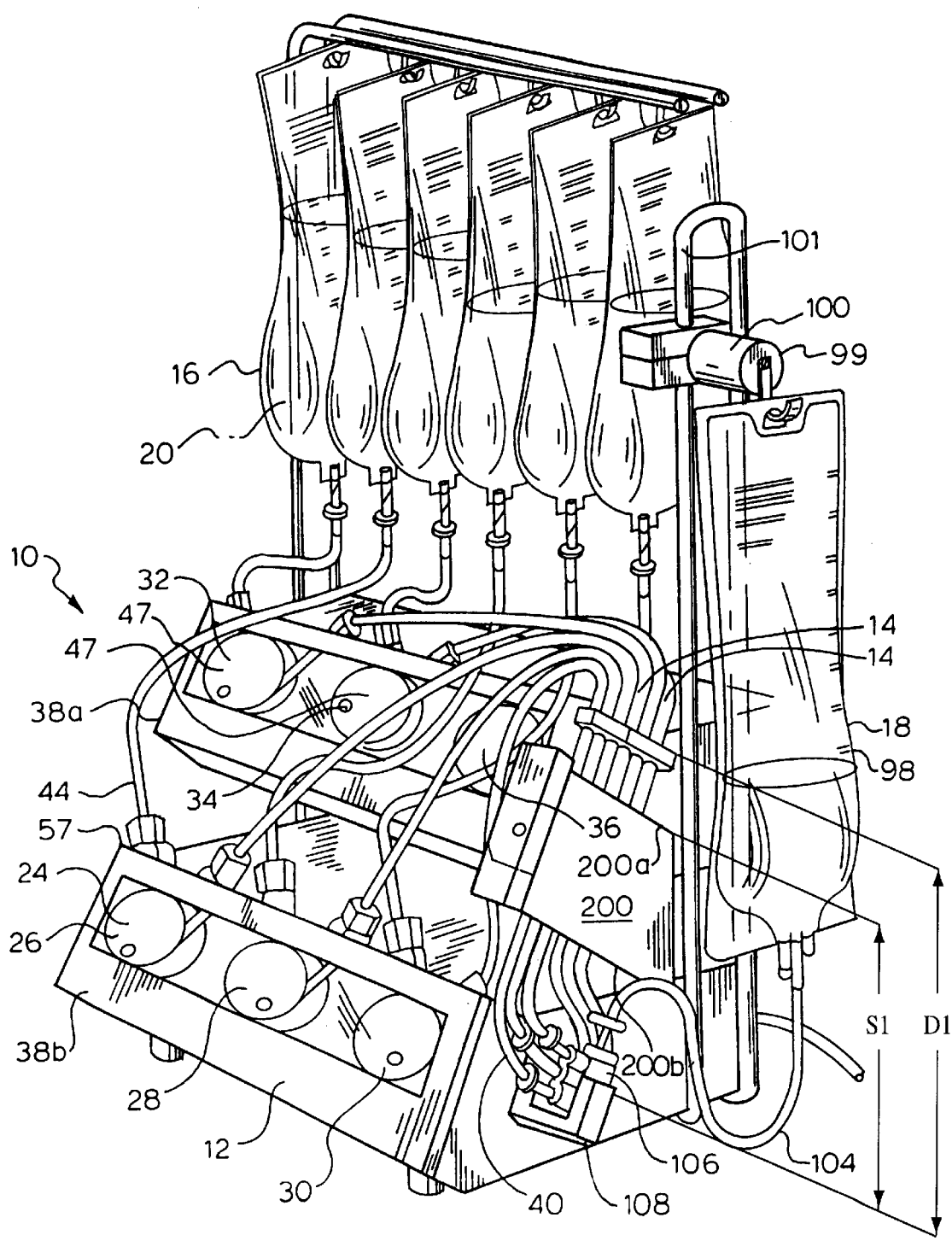
FIG. 1 is a front perspective view of a fluid transfer apparatus forming a part of a preferred embodiment of the present invention.

Referring to FIG. 1, a preferred embodiment of a fluid transfer assembly of the present invention is generally indicated at 10. The illustrated embodiment of the assembly 10 includes a pumping device 12, such as a compounder, examples of which include those compounders set forth in U.S. Pat. No 4,712,590 entitled "ELECTRICAL CONNECTION MEANS FOR MULTIPLE BULK COMPOUNDING SYSTEMS"; U.S. Pat. No. 4,513,796 entitled "HIGH SPEED BULK COMPOUNDER"; and U.S. Pat. No. 5,228,485 entitled "FLEXIBLE TUBING OCCLUSION SENSOR", the disclosures of which are incorporated herein by reference.

The pumping device 12 is shown utilizing a transfer set 14 to place multiple source containers 16 in fluid communication with a receiver or collection container 18. In operation, individual fluids 20 within the source containers 16 are forced by at least one pump 24 forming a part of the pumping device 12, through the set 14 to the receiver container 18. Examples of the receiving container 18 include flexible bags and syringes, among others.

In the preferred embodiment, the pump 24 is a plurality of pumps, preferably six (6) peristaltic pumps 26, 28, 30, 32, 34 and 36 contained within housings 38a, 38b which are placed in a stacked relationship. The transfer set 14 includes conduits 40 formed of flexible tubing 44 arranged to form at least a portion of a fluid passageway 46 (FIG. 4a) from the individual source containers 16 to the receiver container 18. To place the pumps 24 in hydraulic contact with fluid 20 in the tubing 44, a portion of each of the tubing 44 is placed around rollers 47 which form a part of the peristaltic pump 26–36 corresponding to the individual segment.

In operation, the peristaltic pump 24 transfers fluid in a particular source container 16 to the receiving container 18 by selective rotary movement of the rollers 47. This movement causes the pump 24 to hydraulically contact the fluid 20 by compressing the walls of the tubing 44 to place a positive pressure on the fluid, thereby forcing the fluid to flow along the tubing. Other pumps which hydraulically contact the fluid to create the positive pressure include syringe, or volumetric, or cassette pumps among others.

It is also envisioned that the pump 24 may include a pump which hydraulically contacts the fluid by creating a negative pressure on the fluid to force the fluid to flow along the tubing. For example, the pump 24 may create a vacuum in the collection container 18 or an intermediate chamber (not shown) to force the flow of fluid along the tubing 44.

Figure 2:
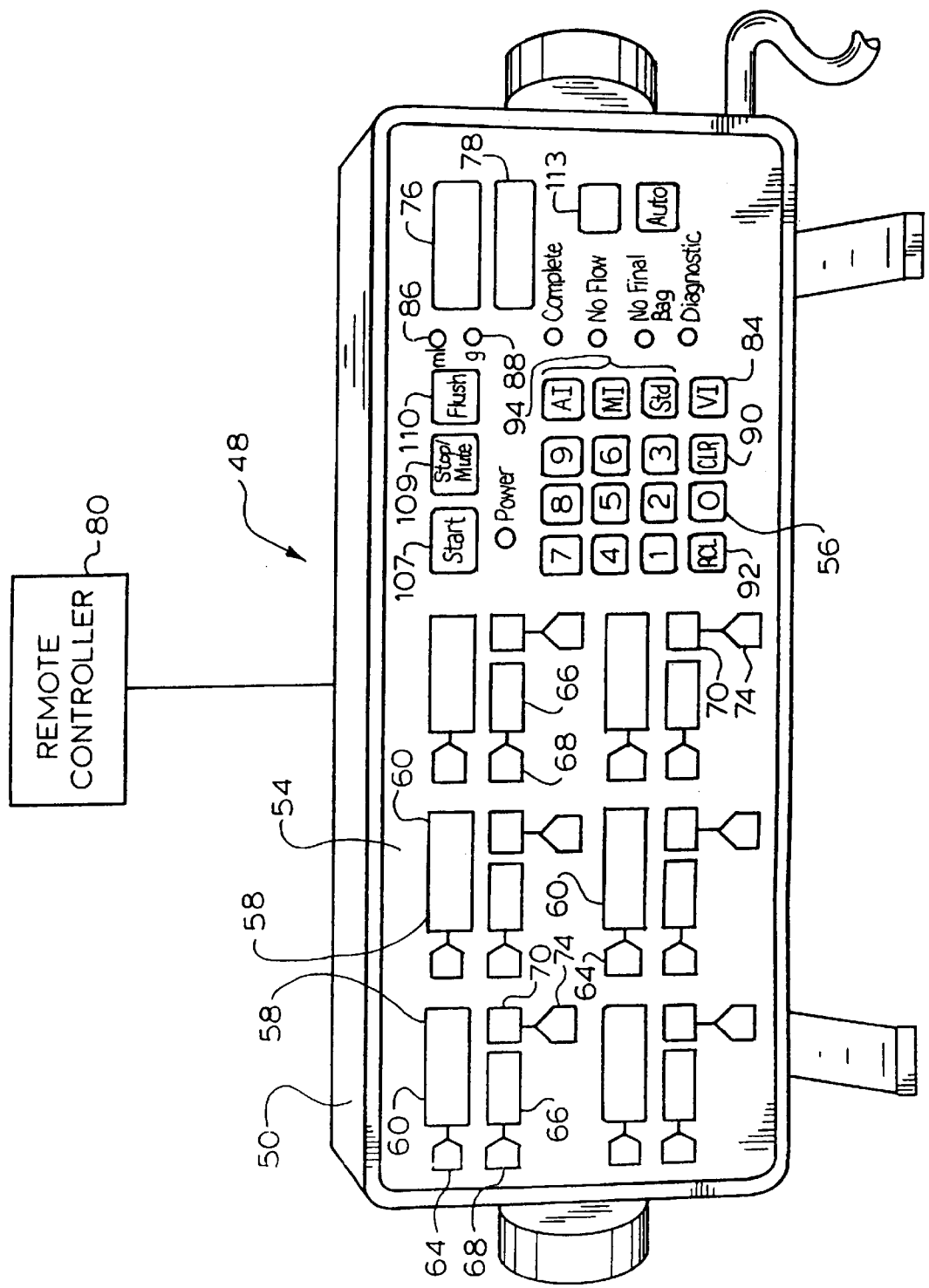
FIG. 2 is a front planar view of a controller within a control panel and forming a part of the preferred embodiment of the present invention.

Referring also to FIG. 2, in the preferred embodiment, each of the peristaltic pumps 26–36 is individually and operatively controlled by a controller indicated generally at 48. Desired quantities of component fluids are transferred by selective operation of the individual pumps 26–36 by the controller 48. The controller 48 controls the pumps 26–36 in at least partial dependence on various inputs and data which may be supplied by various sensors, a separate remote controller or the operator. Preferably the controller 48 is housed within a separate enclosure 50 wired to the housings 38a, 38b but may also be placed elsewhere, such as in one of the housings 38a or 38b (FIG. 1). Generally the controller 48 includes at least one microprocessor connected to various combinations of volatile and nonvolatile memory.

Typically, the panel 54 has an input keypad 56, and a plurality of display stations 58 corresponding to each of the pumps 26–36. Each of the display stations 58 is also associated with one of the source containers 16 and may be color coded for identification purposes. The keypad 56 is a 16 character keypad having digits 0 through 9, a recall key (RCL) and a clear key (CLR) as well as other keys described below.

Also, each of the display stations 58 includes a volume to be delivered display 60 and corresponding entry key 64; a specific gravity display 66 and entry key 68; and a source component family display 70 and entry key 74. The control panel 54 also includes an ID display 76 for the collection container 18 and an alarm display 78.

Referring also to FIG. 2, the values for the volume to be delivered; the specific gravity; and the solution family of fluid from an individual source container 16 may be manually input or input by a remote controller 80.

On one of the display stations 58, the type of component fluid to be transferred by the associated pump 26–36 is entered by pressing the entry key 74 to scroll through the various types on the display 70 until the proper type is shown.

For the volume to be delivered and specific gravity, the proper values are input using the respective entry key 64, 68 and keypad 56. Upon pressing the entry key, the displayed digits flash to indicate the entry mode of operation.

Pressing one of the other entry key 64, 68, 74 enters values which have been input and shown on the station display 58. Entry of a value stops the respective display from flashing. If a value is incorrect, the respective entry key 64, 68, 74 is pressed and then a clear key 90 is pressed to zero out the value, and the entry process is repeated.

As noted above, the input values may also be loaded into the controller 48 by a remote controller 80. An example of such an automatic method and assembly for performing such a method is described in U.S. Pat. No. 4,653,010 entitled "COMPOUNDING SYSTEM" the disclosure of which is incorporated by reference herein. To place the controller 48 in the proper mode for accepting entered input values from either the control panel 50 or remote controller 80 or a combination thereof, a corresponding one of a plurality of mode keys 94 is pressed. The mode keys 94 may include Auto I/D (AI) for when the next patient Identification in a queue is automatically downloaded from the remote controller 80. Another mode key 94 is a Manual I/D (MI) key, to query the remote controller 80 to download input values for a particular patient or prescription. A third mode key, the Standard Mode (STD) key, places the controller 48 into the mode for accepting input values entered using the control panel 50, as set forth above.

When utilizing the remote controller 80, the patient ID may be displayed on the control panel 50 utilizing the volume to be delivered display 60 of one or more of the stations 58. An identification of the collection container 18 may be displayed on the container ID display 76. Other values such as the source or component family fluid identification may also be downloaded by the remote controller. The displayed patient and collection container identification may then be checked against records (not shown). The source component fluid identification may be checked against the source component connected to that station 54 (and pump 26–36 ). If the operator determines that all displayed values are correct, the verify key 84 may be pressed.

Then the input values for the specific gravity and volume to be delivered for one or more of the component fluids 20 which are to be used can be downloaded from the remote controller 80 to the controller 48 and displayed on the station 58 for verification in a similar manner.

Referring back to FIG. 1, the collection container 18 such as a flexible bag 98 is operatively attached to a weighing sensor 99, preferably hung from a load cell 100, which transmits information regarding the weight of the container 18 along with any contents to the controller 48. The load cell 100 may be attached to a bracket 101 forming a part of the pumping device 12. Should the weighing sensor 99 take other forms, such as a scale (not shown), the container 18 may need to be placed on the scale to establish the operative contact.

A transfer tube 104 forming a part of the transfer set 14 may be connected to the collection bag 18 and a junction manifold 106. The junction manifold 106 also places all the tubing 44 from the individual source containers 16 in communication with each other. The ends of the tubing 44 are generally bonded to the junction manifold 106 so that the junction block forms a part of the transfer set 14. In contrast, the transfer tube 104 is removably connected to the junction manifold 106 to allow numerous collection containers to be sequentially filled by connection to a single junction manifold.

A cradle 108 is attached to the housing 38*b* and configured to accept the junction manifold 106 in only a predetermined desired orientation. As described later, the fit between the cradle 108 and manifold 106 promotes proper attachment of the transfer set 14 to the transferring assembly 10.

Forming a part of the transferring assembly 10, is a fluid sensing device or assembly generally indicated at 200. Preferably, the sensing assembly 200 noninvasively provides an indication of the type of fluid within each of the individual tubing 44 in fluid communication with the corresponding source containers 16.

The sensing assembly 200 operates by including, at least partially, a sensing method which is described in a basic form in U.S. Pat. No. 5,612,622, entitled "APPARATUS FOR IDENTIFYING PARTICULAR ENTITIES IN A LIQUID USING ELECTRICAL CONDUCTIVITY CHARACTERISTICS", and more particularly in U.S. patent application Ser. No. 08/762,578, filed Dec. 9, 1996, the disclosures of which are incorporated by reference herein. The preferred method of the present invention includes sensing electrical characteristics of the tubing 44 and contents of the tubing at predetermined times and positions along the tubing and comparing the readings to produce a distinguishing characteristic of the type of fluid within the tubing.

Figure 3:
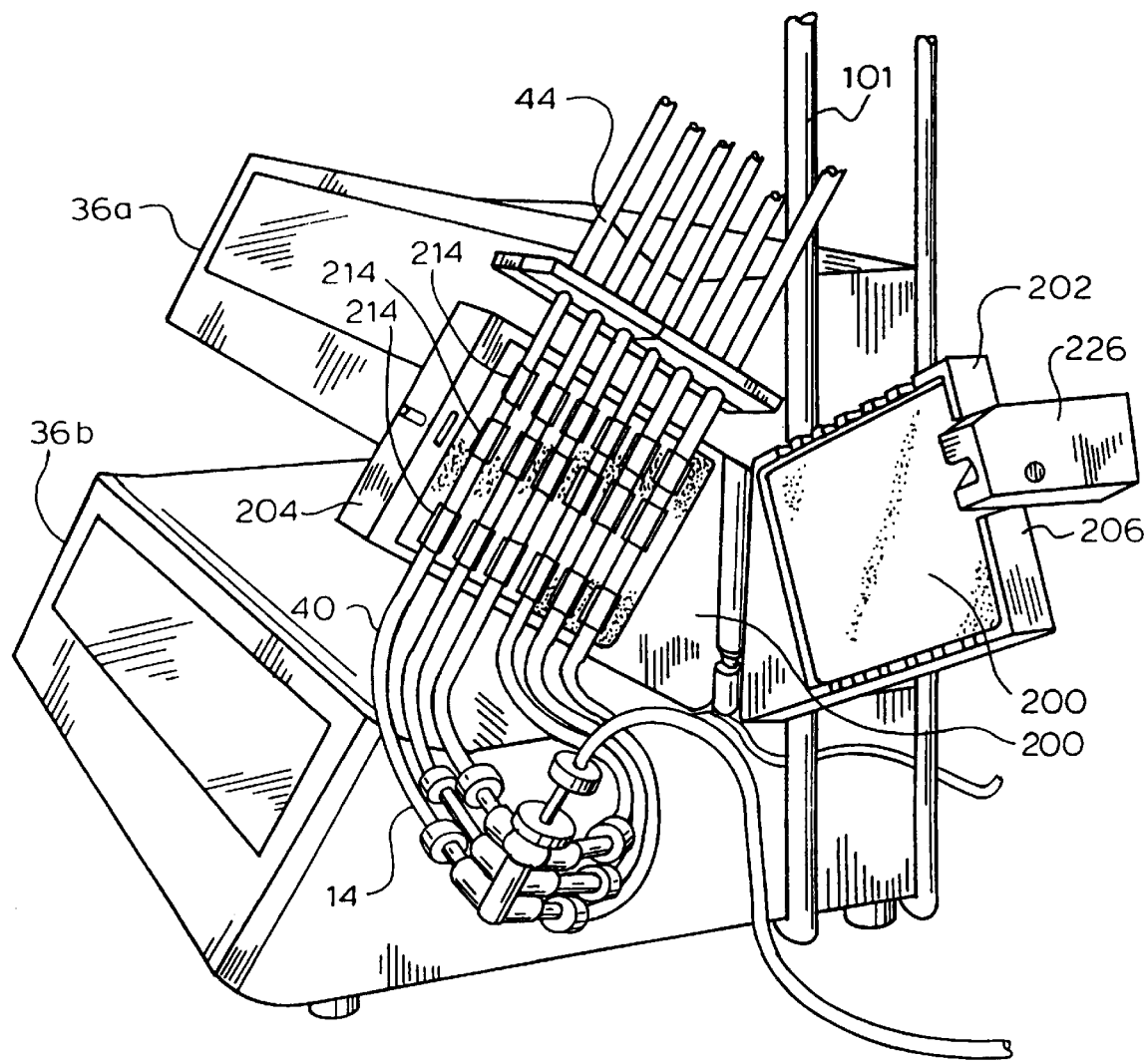
FIG. 3 is a perspective view with parts broken away of the apparatus of FIG. 1 with a sensor block forming a part of the fluid transfer apparatus shown in an open position.
Figure 4:
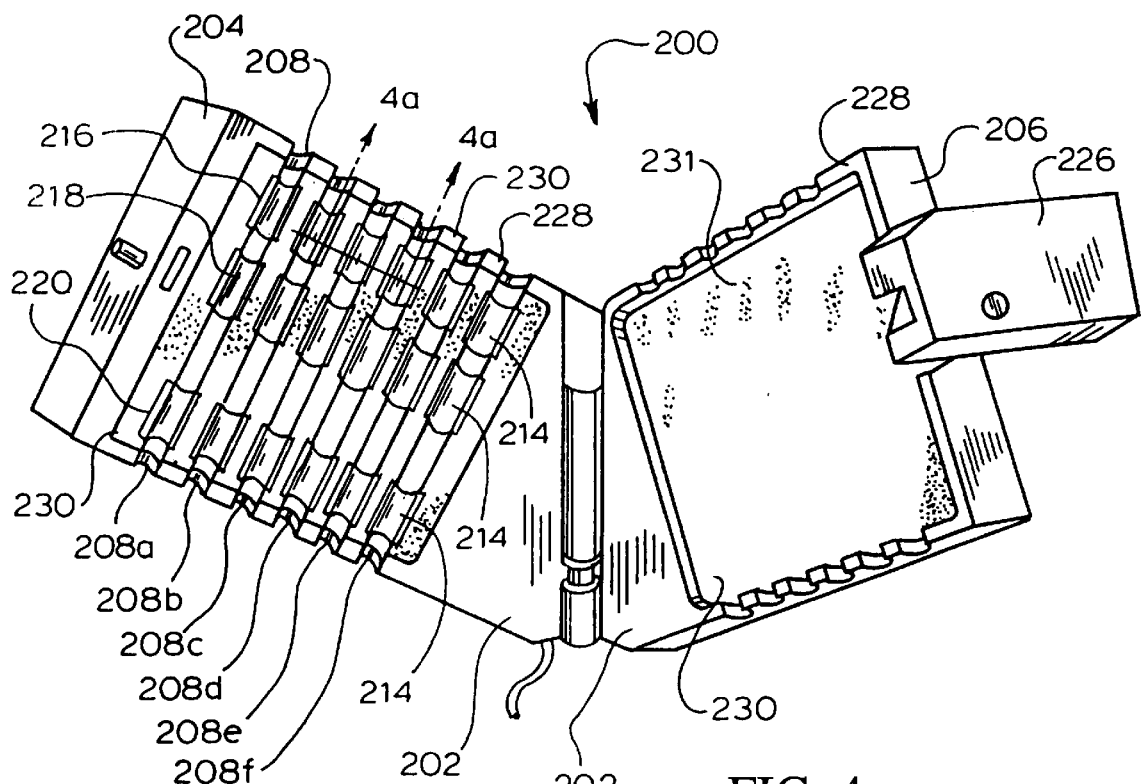
FIG. 4 is an elevational view of the sensor block of FIG. 2 in the open position.

Referring in particular to FIGS. 3 and 4, the sensing assembly 200 includes a housing 202 formed of a base element 204 and a cover element 206 which are attached to each other in a clamshell arrangement. When placed in the closed position (shown in FIG. 1), the base element 204 and cover element 206 define channels 208 (FIG. 4) for receiving at least a portion of the tubing 44. Because it is desirable to sense each of the fluids, tubing 44 from each of the source containers 16 extends through the corresponding pump 26–36 and along a separate channel 208*a–f*. The individual channels 208*a–f* are preferably parallel and arranged along a common plane.

Within the housing 202 and disposed along each of the channels 208 is a plurality of sensing elements indicated generally at 214. A transmitting element 216 is disposed along the top of each of the respective channels 208*a–f*. A first receiving or sensing element 218 is disposed at a first predetermined distance from the first transmitting element 216 and preferably downstream from the first element. A second receiving or sensing element 220 is disposed at a second predetermined distance from the transmitting element 214 and first receiving element 216 and preferably downstream from the receiving element.

A signal is applied by the transmitting element 214 to the tubing 44 and any fluid contents at the transmitting element. The first receiving element 218 and second receiving element 220 detect the signal after the signal has been transmitted along the tubing 44 and fluid contents. By referencing the detected signal vis-a-vis the applied signal, a distinguishing characteristic of the contents of the tubing 44 may be determined.

In the preferred embodiment of the sensing assembly 200, the signal includes a pulse forming a square wave of a predetermined frequency and voltage. This square wave may take on many values such as 5 v at about 39 Kilohertz. The pulse is applied at the first sensing element 216. The first receiving element 218 and second receiving element 220 then acquire the signal. The voltage level of the acquired signal is then sampled at a first and a second discrete time after the applied pulse. By comparing the difference in the sampled voltage between the first and second time periods and the difference in the sampled voltage between the first 218 and second receiving elements 220, the distinguishing characteristic of the type of fluid may be determined. Air or the absence of liquid in the segment 40 of the tubing 44 proximate one or more of any of the sensing elements 216, 220 is also one of the fluids having a distinguishing characteristic which may be pictured by the desired sensing method.

The sensing assembly 200 has the capability to distinguish between an empty tube condition and a no tube condition is beneficial for several reasons. Since either an empty tube or no tube condition result in a highly predictable output from the sensing assembly 200, a diagnostic check to determine if the system is properly functioning can be reliably carried out from time to time, such as when requested by a user or perhaps upon restarting operation after a transfer set has been installed or the assembly is made operational after a shutdown.

Although in the preferred embodiment the sensing elements 214 contact the tubing 44, it is envisioned that the sensing elements may be disposed in other positions and still function to practice the preferred method of the invention. These sensing elements 214 should be in sensory contact with the tubing and contents. The sensory contact includes disposing the transmitting element 216 and receiving elements 218, 220 so that the signal may be transmitted to the tubing 44 and contents and received from the tubing and contents in such a fashion that the distinguishing characteristic may be determined.

In other embodiments other types of signals may also be used. For example, a magnetic field or electrical pulse of a different wave form may also be used.

The sensing assembly 200 is also configured so that each channel 208*a–f* corresponds to one of the pumps 26–36. Thus, fluid pumped by a particular one of the pumps 26–36 is to flow through tubing received in the particular corresponding channel 208*a–f*.

However, it has been found that in compounding nutritional solutions for patients, there may be types of source solutions for which the characteristic of the fluid given by the described distinguishing method may not be as distinct as desired to distinguish between the solutions. For example, high concentration dextrose solutions and a solution containing branched chain amino acids may exhibit similar characteristics when exposed to the detection method. Therefore, for some fluids exhibiting similar characteristics it may be advantageous to supplement the detection method with an additional second method which distinguishes between such fluids.

One such second method is to distinguish between fluids by examining the flow rates of the fluids while the fluids are being pumped. Fluids frequently possess distinguishing physical characteristics which along with the hydraulic flow resistance found in the transfer set 18 have an effect on the flow rate of the fluid within the set. The junction manifold 106 is an example of a portion of the transfer set 14 which forms hydraulic flow resistance for the flow of fluid through the set.

For example, as may be appreciated, dextrose has a higher viscosity than a fluid containing branch chain amino acids. Thus, under similar pumping conditions, the flow rate of dextrose through the transfer set 14 will typically be lower than the flow rate of the source fluid containing branch chain amino acids.

Referring also to FIG. 1, one way the flow rate differential can be indicated is by a novel use of the weight change per unit of time of the collection container 18 as sensed by the weight sensor 99 and which occurs during pumping. By way of example, because the pumps 26–36 exhibit similar pumping characteristics, the flow rate of each of the fluids 20 through the transfer set 14 depends at least partially on the viscosity of that fluid. This variation in flow rate will be, at least partially, indicated in the difference between the weight gain per unit of time for the container 18 as it receives one type of component fluids 20 versus a second type of component fluid. Thus, the change of the weight of the container 18 per unit of time during pumping will, in many instances, vary between the various fluids, which gives an indication of the flow rate differential and thus the type of the fluid going into the container.

One particular advantage of using the sensor assembly 200 and weighing sensor 99 in the method described above, is that the identification of the fluids is accomplished by sensing devices which do not require contact with the fluid to function properly. In fact, a disposable transfer set 14 is easily accommodated by these sensing devices.

Referring back to FIGS. 3, 4 and 4a and turning now to the above-identified sensing assembly 200 in greater detail, the housing 202 is attached to the upper housing 38a (FIG. 1). The housing 202 (FIG. 3) is preferably placed at an angle relative to horizontal to facilitate placement of the tubing 44 within the housing and opening of the housing about the bracket 101. The housing 202 includes a latching assembly 226 to retain the base element 204 and the cover element 206 in the closed position (shown in FIG. 1).

Figure 4A:
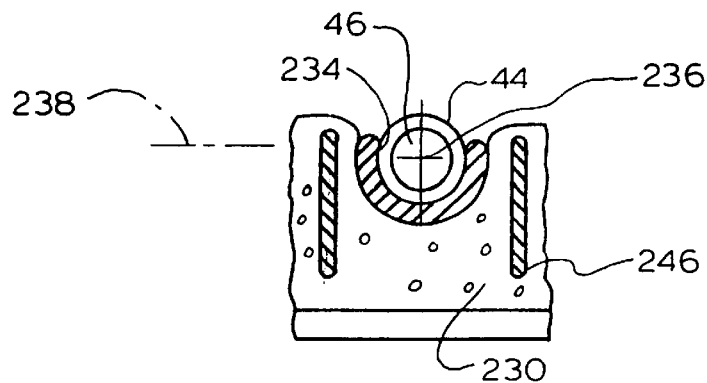
FIG. 4a is a partial cross sectional view of the sensor block taken generally along line 4a—4a in FIG. 4.

Referring to FIGS. 4 and 4a, both the base element 204 and the cover element 206 of the housing 202 include an outer shell 228 and an inner element 230. Preferably, the channels 208 are defined in the inner element 230 of the base 204 while the surface 231 of the inner element 230 of the cover 206 is generally planar. In alternate embodiments, a portion of the channel 208 may be defined in the inner element 230 of both the base 204 and cover 206.

Disposed along each of the channels are the transmitting element 216, the first receiving element 218 and the second receiving element 220. To facilitate manufacture and assembly, all of the sensing elements 214 are similarly formed. In the preferred embodiment, the sensing elements 214 are formed as a tubular segment having a "C" shaped cross section and an inner surface 234 forming an interior into which a portion of a length of the tubing 44 is inserted.

In cross section particularly shown in FIG. 4a, the inner surface 234 is generally circular and is sized to snugly fit about the tubing 44. The element 214 is formed so that a central axis 236 of the tubing 44 is interior of, or recessed relative to, a plane 238 defined by edges 240 of the inner surface 234 disposed directly opposite the tube 44. Thus, the element 214 preferably envelopes a majority of the circumference of the tube. It has been found that the tubing can be easily inserted into an opening defined by the edges 240 with the elements then removably clutching the tubing which promotes intimate contact between the sensing elements and tubing. Such contact facilitates the operation of the sensing assembly 200.

To minimize pinching or gouging of the tubing 44 by the elements 214, the outer edge 240 of the element is formed with a smooth radius. It has also been found that the surface texture of the inner surface 234 affects the elements 214 in transmitting or receiving the signals.

Although the separation between the elements 214 along a channel 208 may vary, in the preferred embodiment the transmitting element 216 is separated from the first sensing element 218 by approximately 0.2 inches, while the second sensing element 220 is separated from the transmitting element 214 by approximately 1.6 inches.

To isolate the elements from potential electrical interference, the inner elements 230 are composed of an electrically nonconducting polymer and the assembly 200 includes generally planar shields 246 preferably is an electrical conducting material which extend within the inner elements and generally parallel to the channels 208 and along both sides of each of the channels. It has been found that similar shielding is not necessary between the elements 216, 218 and 220 disposed along one of the channels 208.

It is also envisioned that the sensing assembly 200 may be adapted so that the transfer tube 104 may also be passed through the sensing assembly. The sensing assembly 200 may then sense the contents of the transfer tubing. Such an arrangement may however, lead to nuisance alarming as the transfer tubing 104 will likely contain fluid from a previous pumping cycle upon the initiation of a second pump 24. Thus the controller 48 may find a mismatch. A delay may be incorporated to reduce this nuisance alarming.

Figure 5:
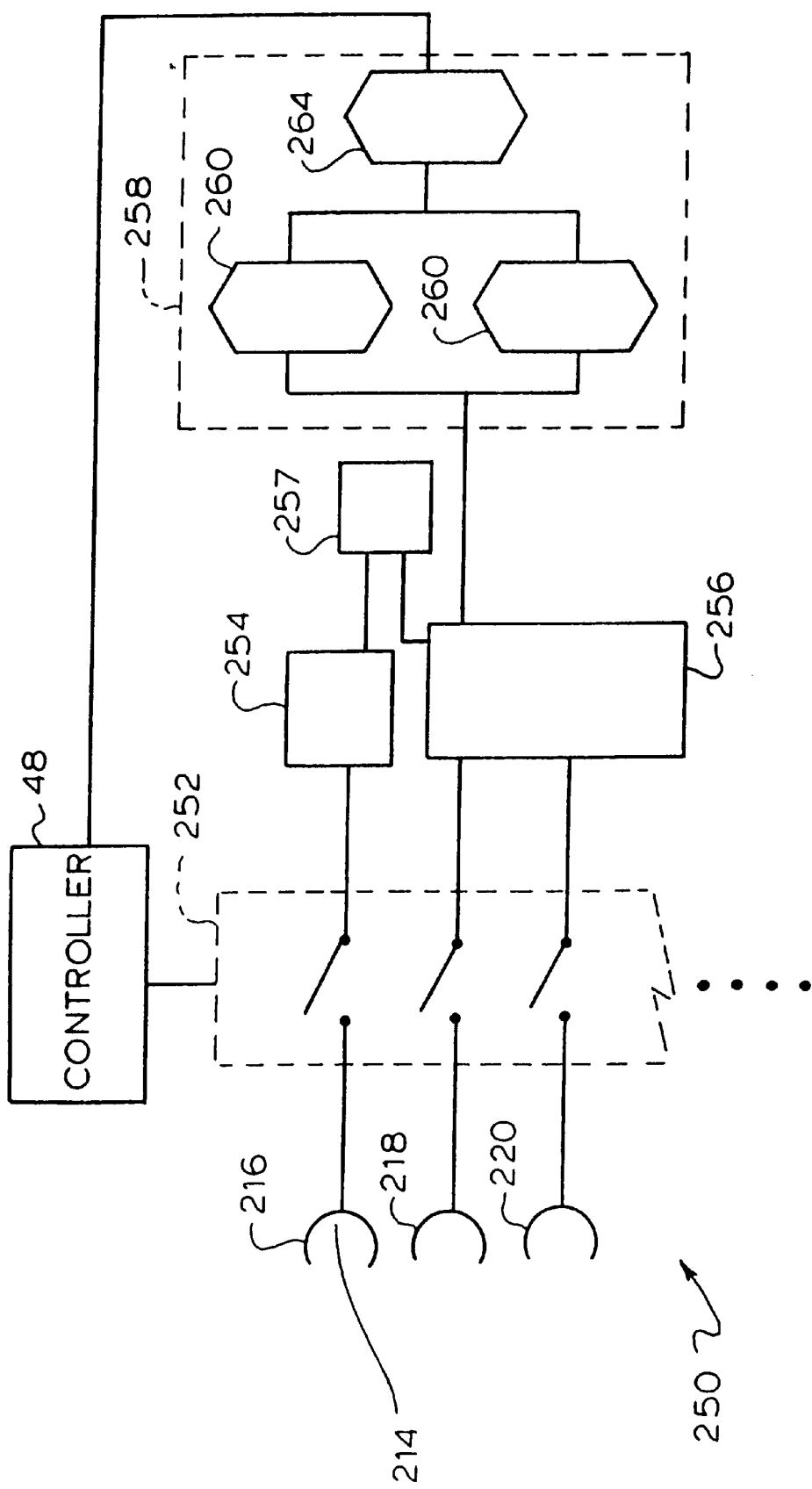
FIG. 5 is a schematic block diagram generally representing a portion of the control and operating system of the fluid transfer apparatus shown in FIG. 1.

Referring to FIG. 5, a block diagram illustrates the general layout of a preferred embodiment of the circuit, indicated generally at 250, forming a part of the sensing assembly 200. The controller 48 actuates a switching circuit 252 to activate the sensing elements 214 along a desired channel 208 to sense the fluid in the tubing 44 extending along that channel. The circuit 250 is preferably housed in the base 204 (FIG. 4). For example during operation of one of the pumps 24 (FIG. 1), the controller 48 actuates the channel 208a–f corresponding to that pump. The controller 48 generally actuates the sensory assembly 200 at predetermined times.

Upon actuation of the sensing elements 214 for the desired channel, a signal generator 254 supplies a signal, preferably a pulse consisting of a square wave of a predetermined frequency and voltage to the transmitting element 216. The signal is then transmitted by the transmitting element 216 into the tubing 44 (FIG. 1) and the contents of the tubing.

The signals received at the first receiving element 218 and second receiving element 220 are amplified and transmitted to a sampling circuit 256 which under the direction of a timing circuit 257 samples the amplified signals at predetermined times, preferably two separate times, relative to the transmitted signal.

The sampled signals are then transmitted to an analyzing circuit 258. In the preferred embodiment, the analyzing circuit 258 is composed of at least one and preferably two initial lookup tables 260, where the sampled signals from the first element 218 and second element 220 are compared to stored value ranges representative of tubing containing known source solution types. Output from the initial lookup tables 260 is transmitted to a second lookup tables 264 which also compares the signals to stored value ranges representative of known source solution types. At least one of the initial lookup tables 260 and second lookup table 264 contains a stored value range corresponding to a tube containing air and the sampled signals are also compared to this range.

If the signals fall within the value ranges stored in at least one of the initial lookup tables 260 and second lookup tables 264, a code representative of the corresponding compound fluid type is transmitted to the controller 48. If the signals do not fall within the stored value ranges, an indicative code is returned to the controller 48. If the code indicative of any unidentified fluid type is received, the controller 48 preferably generates an alarm.

Many of the operational steps of compounding a solution are described in the U.S. Pat. Nos. 4,653,010 and 4,513,796 noted above, with the disclosures of these patents incorporated by reference herein. The present invention, however, significantly enhances the efficacy of these described methods.

For example, upon starting of the pumping device 12, the controller 48 will check the specific gravity for each of the fluids being pumped by the pumping device with the range of specific gravity for that type of fluid. As noted above, the specific gravity and fluid solution type are both input into the controller 48 for each of the fluids to be pumped. The controller 48 also contains ranges of specific gravity values for the different types of component fluids 20. Upon pushing of the start button 107, the controller 48 compares the specific gravity input into the controller for each of the fluids which are to be pumped by the pumping device 12 to the stored range of specific gravity for that component fluid type. If the input specific gravity does not fall within the stored range, an alarm will sound and the station 58 having the mismatched specific gravity will blink.

Figure 6:
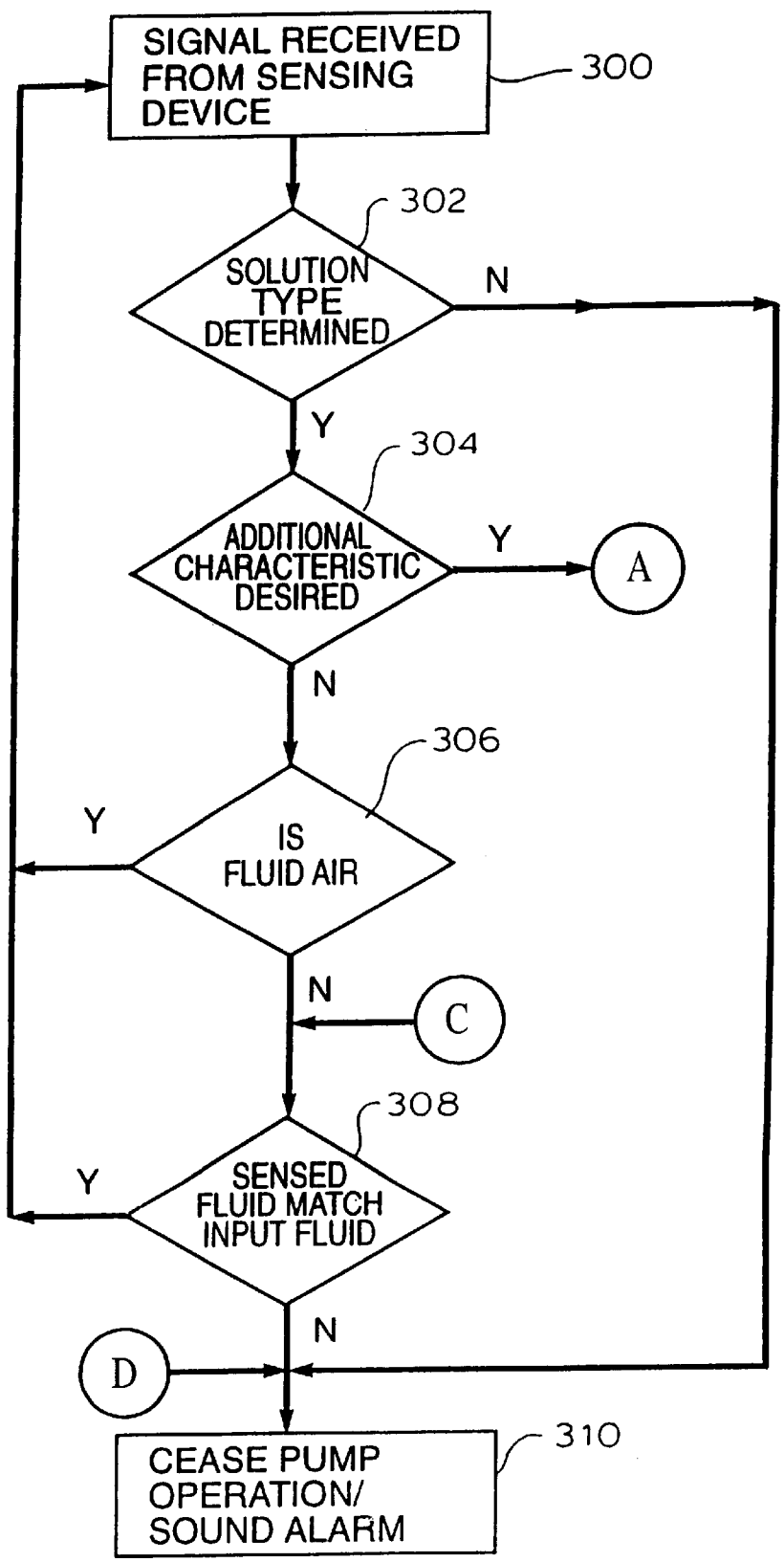
FIG. 6 is a flow chart illustrating at least part of a preferred method for identification of a distinguishing characteristic of a component fluid which is to be transferred by the apparatus of FIG. 1.
Figure 7:
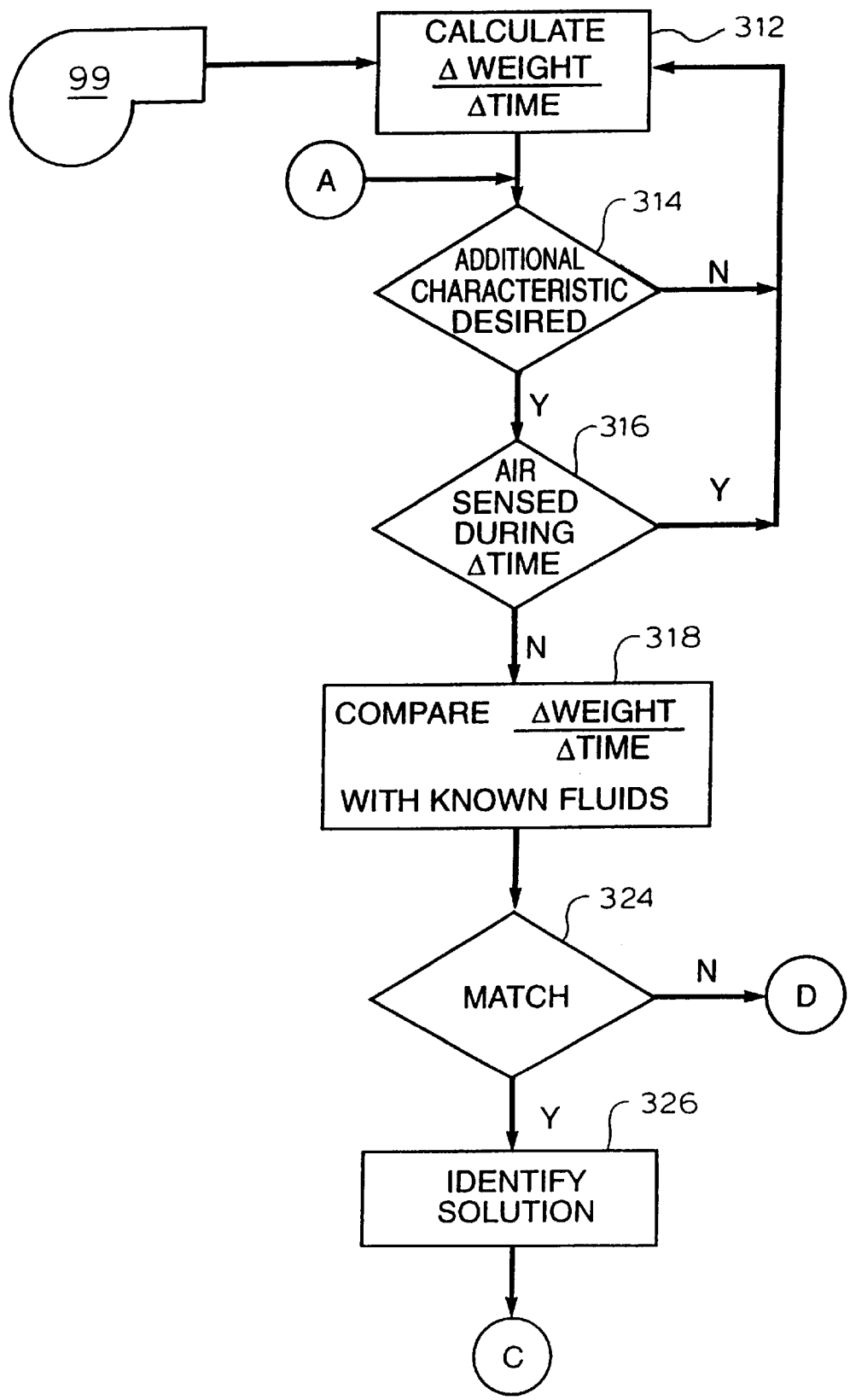
FIG. 7 is a flow chart illustrating at least part of a preferred method for identification of a second distinguishing characteristic of a component fluid which is to be transferred by the apparatus of FIG. 1.

Referring to FIGS. 1, 6 and 7, a preferred method for utilizing the sensing assembly 200 and weight sensor 99 (FIG. 1) is illustrated. The sensing assembly 200 supplies a signal to the controller 48 (FIG. 2)indicating the type of fluid within the segment of tube 44 extending through the housing 202, as illustrated by block 300 in the figure.

The controller 48 then determines if the signal indicates that a solution type was identified by the sensing assembly 200 as shown in decision diamond 302. If the solution type was not identified, the controller 48 stops operation of the fluid transfer assembly 10 and sounds an alarm. Referring briefly to FIG. 2, the alarm may be muted by pushing a stop/mute button 109 on the control panel 50.

As illustrated by decision diamond 304, if the solution type is identified by the sensing assembly 200, the next step is to determine if the sensed fluid type is one of those types of fluids, for example dextrose and branch chain amino acids, for which an additional distinguishing characteristic is desired.

If the additional distinguishing characteristic is not desired, a determination is made whether the sensed type of fluid is air. If the sensed type of fluid is air, as represented by decision diamond 306, the assembly 10 continues in a normal operation and the process is repeated by the supply of the next signal 300 from the sensing assembly.

If the sensed fluid is not air, a comparison is made between the sensed type of fluid and the type of fluid which is to be expected from the source container 16 which is connected to the tubing 44 being sensed, as illustrated by decision diamond 308. The type of fluid in that source container 16 and which is to be transferred by the pump 26–36 corresponding to the channel 208a–f had been previously input into the controller 48, as described above. If the sensed type matches the input type, the compounder 12 continues in a normal operation and the process is repeated by the supply of the next signal 300.

If, however, the sensed type of fluid does not match the input type of fluid, the respective pump 24 ceases operation, and an alarm is sounded and displayed on the front face of the panel 54 (FIG. 2), as represented by block 310. The display of such an alarm state, is preferably achieved by blinking the displayed digits on the corresponding display station 58 for that fluid and an error message such as "incorrect solution" is displayed on the error display 78.

Referring to FIGS. 1 and 7, during pumping and using input from the weighing sensor 99 the change of weight of the container 18 and contents of the container over a predetermined time interval is repeatedly calculated by the controller 48. It has been found that a time interval of 3 seconds provides satisfactory results, although other time intervals may also prove satisfactory. The change of weight calculating step is represented by block 312.

Based on the input supplied by decision diamond 304, the controller 48 determines if the additional identifying characteristic for the fluid identified by the sensing assembly 200 is desired, as indicated by decision diamond 314. If no additional characteristic is desired, the controller returns to the weight change calculating step.

If the additional characteristic is desired, a determination is made as to whether the sensing assembly 200 has detected air in the tubing over the predetermined time interval during which the change of weight has been calculated. This air detection step is represented by decision diamond 316. As can be appreciated, air flowing within the tubing 44 may cause the change of weight of the container 18 and contents to be different than that which would have occurred had there been liquid flow during the entire period. Thus, the weight change may not be indicative of the flow rate of a particular liquid.

If air in the tubing 44 is detected during the time interval over which the change of weight of container 18 is examined, the controller returns to calculating the change of weight per unit of time.

If air has not been detected, the controller 48 compares the weight change with a lookup table of weight changes for a comparable unit of time for various potential component fluids, as represented by block 318. As indicated by decision diamond 320, if the weight change is within a range of stored weight change values for a particular source solution which matches one of the possible source solutions as indicated by the sensing assembly 200, that type of solution is identified, as indicated in block 326, otherwise an alarm is returned.

Referring also to FIG. 6, the identified solution is then compared with the input solution type as represented in decision diamond 308, described above. If there is no match, the assembly 10 ceases operation and the alarm is sounded. If there is a match, the assembly continues normal operation.

Thus it can be seen, that the controller 48 forming a part of the mixing assembly 10 utilizes inputs from the sensing assembly 200, and possibly the weighing sensor 99 to distinguish or identify the type of solution flowing through the particular tubing 44 and into the collection container 18. The identified solution is then compared with or checked against the solution type which has been input into the controller 48 for a particular pump 26–36, typically by the operator or remote controller 80. If the types do not match, an alarm condition is sounded and the assembly 10 ceases operation.

Other methods of sensing an additional distinguishing characteristic of the transferred fluid are also included in the present invention. For example the operation of a volumetric pump may be dependent on the type of fluid being pumped. Thus by monitoring the operation of the pump, the additional characteristic may be identified.

Referring to FIGS. 1 and 3, it should be understood that the controller 48 may be remotely located relative to the housings 38a and 38b. Signals may be transmitted by a number of ways between the sensing assembly 200, the controller 48, the load cell 100 and the housings 38a and 38b. Hard wiring is one such way. Another envisioned way is by infrared or radio transmission. Also, the controller 48 may be configured to directly output or cause the output of the signal to the transmitting electrode 216 and read the signal detection inputs from the receiving electrodes 218, 220. The controller 48 may then perform the identification method on the respective signals.

In the preferred method, upon the initial starting of the assembly 10, the sensing assembly 200 identifies the fluids within all of the tubing which extend through the channels 208. Because the fluid within a particular tubing 44 may not be flowing initially, flow rate identification is not performed. The types of solutions identified by the sensing assembly 200 are compared with the input types of solutions for the corresponding pumps 26–36 and an alarm is sounded if a mismatch is found.

Because there is no flow at start up, if the solution identified by the sensing assembly 200 is one for which the second identification method is normally performed, that second method is not performed and instead the controller 24 checks the indicated solution type against the plurality of possible solution types. If a match is found among the plurality, the assembly 10 continues normal operation.

After initial start up and fluid is being pumped through the tubing 44, the controller 48 identifies the fluid or air in the tubing 44 through which a fluid is flowing, using inputs from both the sensing assembly 200 and, if necessary, the weight change as detected by the weighing sensor 99, as described above. The identified solution type is then matched against the input solution type.

If a mismatch is found, either during initial startup or subsequent operation, the alarm is sounded. The operator then checks to insure that the proper source container 16 is connected to the station 58 displaying the alarm condition. The operator may also check to see if the right solution type has been input into the station 58.

In the preferred method of operation of the present invention includes examining the input from the weight sensor 99 only when the sensing devices 200 determines that the type is one or more of a subset of possible solution types. In other embodiments, the present invention may also include utilizing the input from the weighing sensor 99 regardless of the solution type sensed by the sensing device 200.

It is envisioned that there may be instances where the source solution is correct, and the type of solution may be input correctly into the system, and yet the controller 48 generates a solution mismatch alarm. One example of such an occurrence, is when the source solution container 16 having a particular solution type is correctly replaced with a container having another type of solution, and the new input solution type is correctly input into the controller 48. Fluid from the first solution type may still be in the tubing 44 with the old solution being sensed by the sensing assembly 200, thereby generating the alarm.

Referring to FIGS. 1 and 2, to overcome such an alarm, the transfer set 14 is flushed by depressing the flush switch 110 on the front face 54 of the control panel 50. The pump 26–36 corresponding to the alarming station is activated for a brief period or until the new solution is detected, to flush the tubing 44. If the correct solution type is then identified, the compounding may be restarted. The collection container 18 is then discarded, as indicated to the controller 48 by the removal of the weight from the load cell 100. A new collection container 18 is then hung from the load cell 100, and the compounding process is restarted.

The controller 48 may also be configured so that it compares the contents of the tubing 44 relative to the operation of one of the pumps 26–36 to sense a free flowing condition. For example, if the controller 48 receives from the sensing assembly 200 designating an empty tubing 44 and then at a later reading receives a code designating liquid in the tubing without the corresponding pump being in operation, a free flow condition may be identified.

Figure 8:
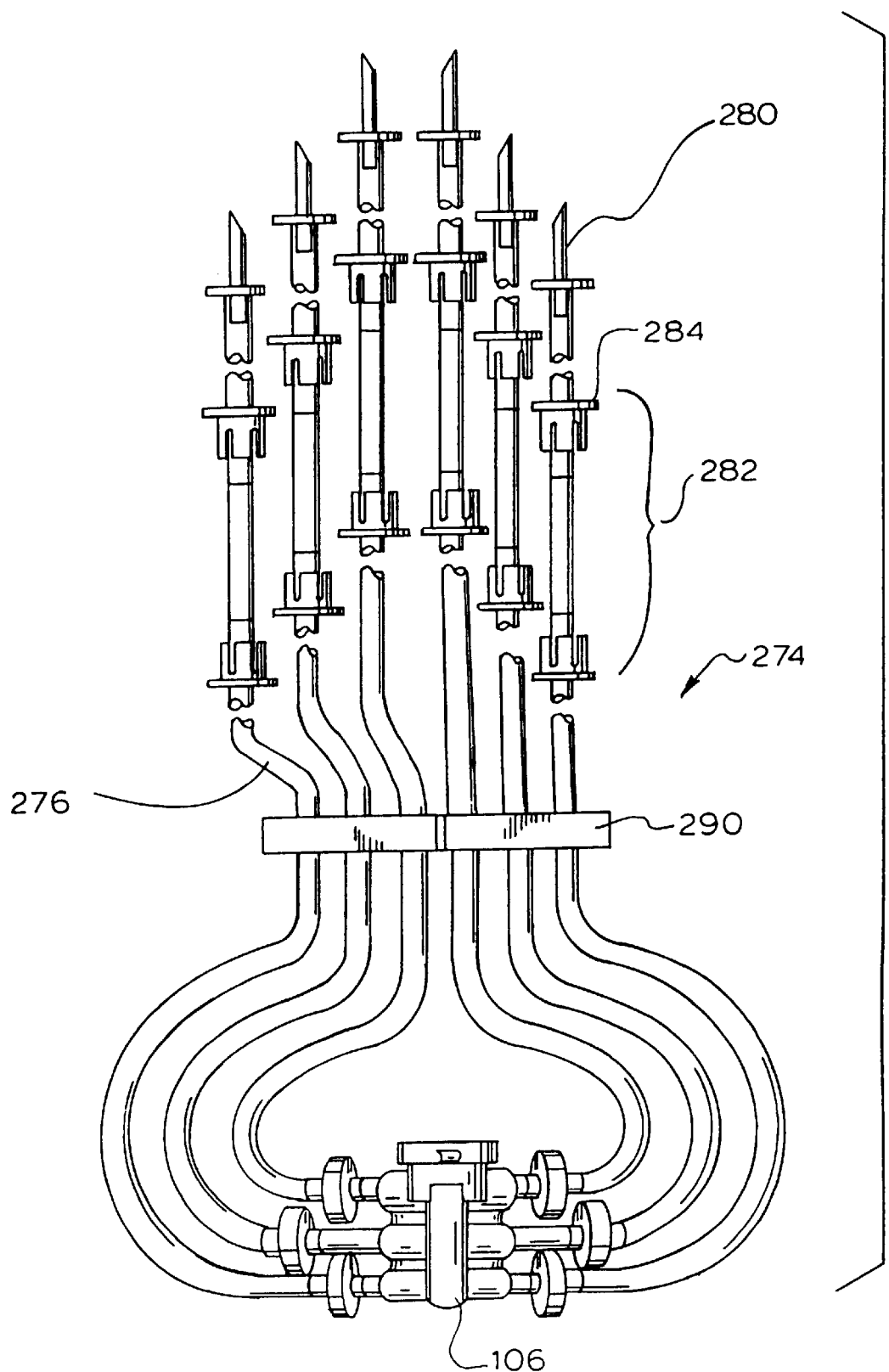
FIG. 8 is a preferred embodiment of a transfer set adapted for use with the transfer apparatus of FIG. 1.

Referring to FIG. 8 in conjunction with FIG. 1, the preferred embodiment of a combining portion 274 of the transfer set 14 which finds particular application with the compounder 12 and sensing assembly 200 is illustrated. The combining portion 274 includes a plurality of tubing segments 276, One end of each of the tubing segments 276 may be connected to one of source container 14. Preferably, attached to one end of the tubing 276 are connectors 280 for removably connecting to source containers 14. In the preferred embodiment, the connectors 280 are spikes for accessing ports forming a part of a flexible solution container.

An intermediate portion 282 of the tubing segments 276 is uniquely configured for operative attachment to one of the pumps 24 and includes retainers 284 to maintain the operative attachment between the tubing 276 and pumps during operation. To facilitate the proper attachment of the transfer set 14 to the compounder 12, the connector 280 and retainers 284 on a particular one of the tubing segments 276 are color coded to match the color coding on the display station 58 on the control panel 50. The color coding is also applied to an entry port 57 of the pump 26–36 that is operatively connected to a single color coded display station 58.

The opposite ends of each of the tubing 276 are connected to the junction manifold 106. As can be appreciated, ensuring that a tube extending from a particular pump 26–36 is threaded through the proper channel 208 is important or there will be a mismatch between the fluid sensed by the sensing assembly 200 and the type of fluid input for that particular pump.

Figure 9:
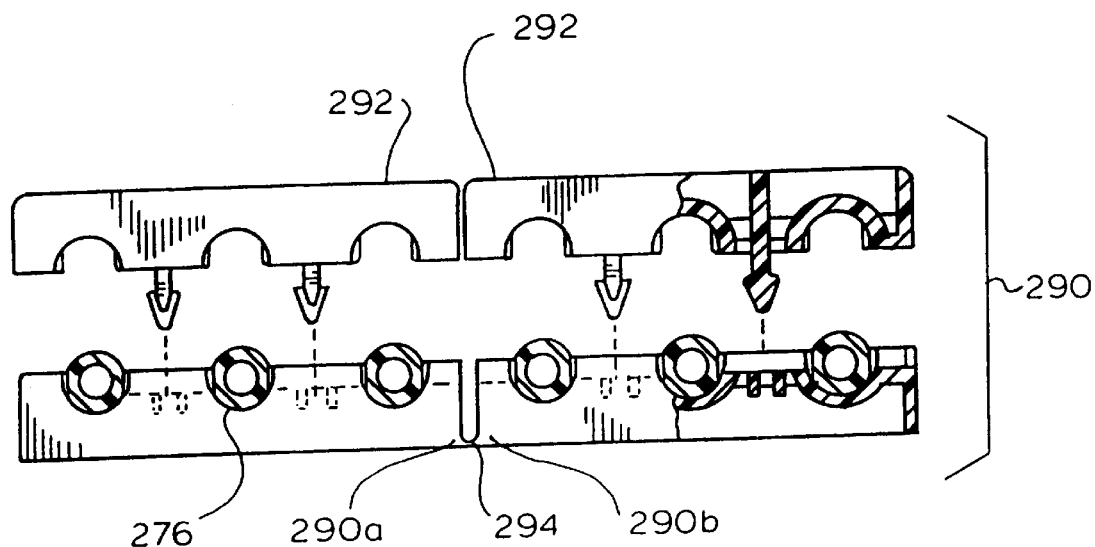
FIG. 9 is a top planar view with parts broken away of a bracket forming a part of the transfer set of FIG. 8.
Figure 10:
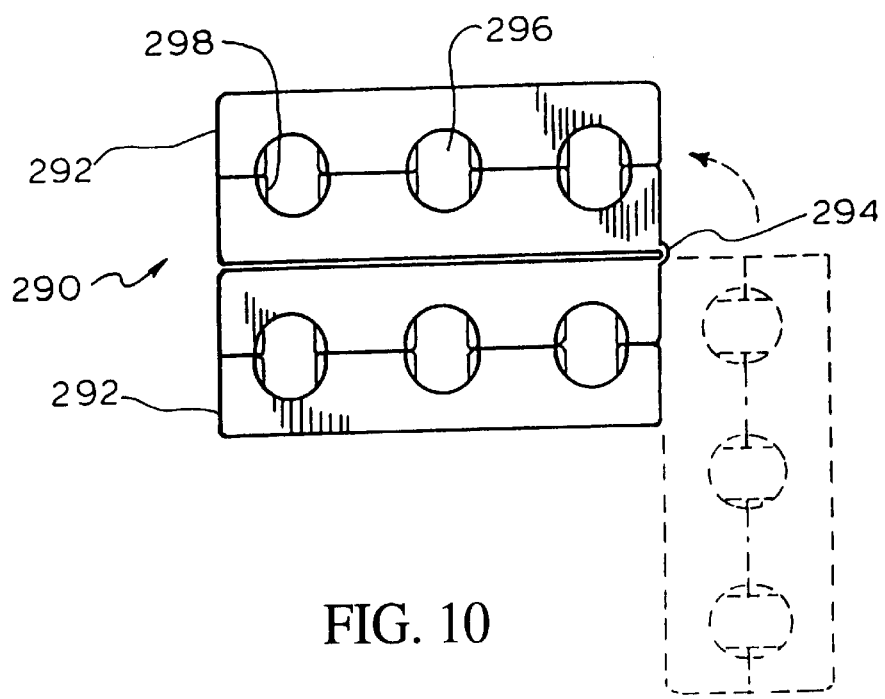
FIG. 10 is a top planar view of the bracket of FIG. 8 illustrating the movement of the bracket.

Referring also to FIGS. 9 and 10, to arrange the various tubing 44 so that the individual tubing is placed in the proper corresponding channel 208a–f a bracket 290 is provided. The bracket 290 retains the individual tubing segments 276 in a predetermined arrangement relative to each other. The bracket 290 preferably is formed as two similarly configured portions 292 holding an equal number of tubing. The portions 292 are connected to each other by a living hinge 294 attached to a rear corner 292a of one of the portions 292 and the opposing rear corner 292b of the other portion.

The hinge 294 allows the bracket 290 to fold so that the portions 292 extend along each other to facilitate packaging of the combining portion as particularly shown in FIG. 10.

In addition, the hinge 294 allows the portions 294 to be unfolded to a position where the portions are generally aligned with each other and an abutting interference between the two portions 292 prevents further unfolding as shown in FIG. 9. The bracket 290 forms passageways 296 for the tubing 276. Opposing teeth 298 are formed within the passageways 296 to clamp the tubing 276 and prevent slippage of the tubing 276 relative to the bracket 290.

The bracket 290 is important in facilitating the attachment of the connection portion 274 of the transfer set 14 to the pumping device 12. As noted previously, each of the channels 208 (FIG. 4) corresponds to a particular pumping station 26–36 to which a component fluid 20 has been identified by input to the controller (FIG. 2). If the proper tubing segment 276 is not inserted into the proper channel as the component fluid flows through the tubing and improper channel 208 where the fluid is sensed by the sensing assembly 200, a nuisance alarm will be generated.

The bracket 290 makes it very difficult to inadvertently place the wrong tubing segment in a channel 208. The bracket 290, in the unfolded position aligns the tubing segments 276 in the proper order relative to each other. In addition, in the preferred embodiment the bracket 290 is placed at a predetermined distance d1 from the junction manifold 106 along the tubing segments 276. This distance d1 is set by the spacing s1 between the cradle 108 an at least one of the upper edge 200a or lower edge 200b of the sensing assembly 200. Preferably the distance d1 is set by the spacing between the cradle 108 and upper edge 200a so that when the junction manifold 106 is placed in the cradle 108, the tubing segments may be extended so that the bracket just clears the upper edge.

As noted earlier, the cradle 108 and junction manifold 106 are configured so that the junction manifold can be received in the cradle in only a desired orientation. When the junction manifold 106 is placed within the cradle 108 and the tubing segments 276 between the bracket 290 and junction manifold are extended so that the bracket clears the upper edge 200a, the proper alignment of the tubing segments becomes self evident. Orienting the bracket 290 in the opposite direction, causes a corkscrewing of the tubing which reduces the effective length of the tubing so that the junction manifold 106 cannot be received in the proper orientation in the cradle 108. In addition, a sideways displacing of the bracket 290 relative to the sensing assembly 200 in either direction, will cause at least one of the tubing segments 276 to not be received in a corresponding channel 208. This "orphaned" tubing segment will then interfere with the closing of the sensing assembly which indicates the misplacement.

The operation of the preferred embodiment is carried out utilizing the controller 48 which implements the above described operations which have been generally described and described in connection with the flow charts of FIGS. 6 and 7. The general overall operation is carried out according to the flow charts shown in FIGS. 11–24 which will be generally described, followed by specific functionality that represents important aspects of the present invention.

Figure 11:
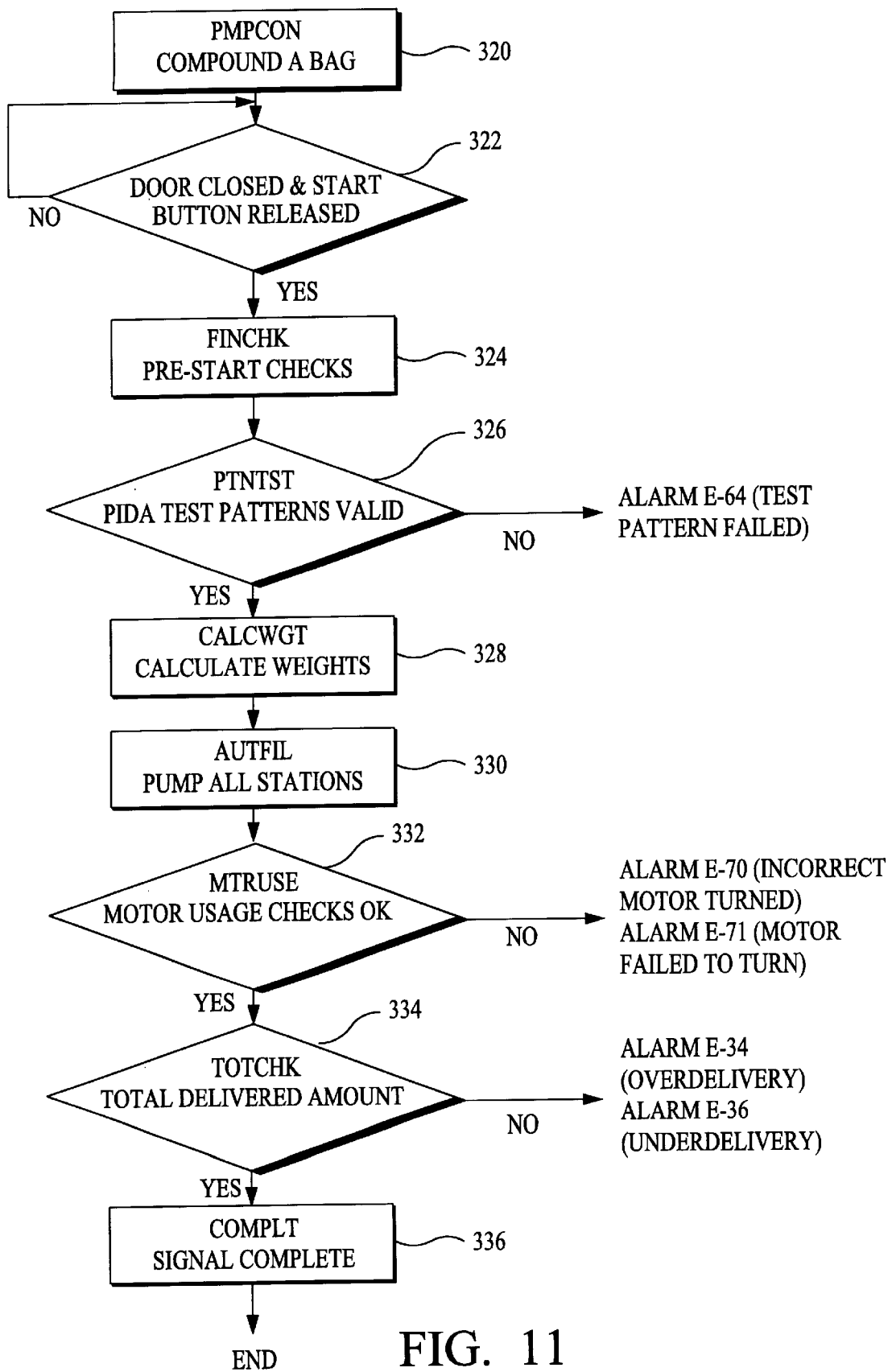
FIGS. 11 through 26, 27A, 27B, 28A and 28B together represent flow charts illustrating operation of a preferred embodiment of the fluid transfer assembly of the present invention.

Turning now to FIG. 11, when the assembly is to compound a bag (block 320) the user closes the door and depresses and releases the START button (block 322). Prestart checks (block 324) are performed, including pressing a FS check pushbutton 113 shown in FIG. 2 when no transfer set is installed in the compounding assembly. This should produce a known result by the sensing assembly which is an indication that the compounding assembly is operating properly. A transfer set is then installed, and another FS check is done, which should also yield a known result indicating an empty tube reading. If the sensing assembly continues to produce a no tube reading for one of the channels 208, an install alarm may be generated to indicate to the user an incorrect or no installation of the transfer set 14 in the sensing assembly 200. While these tests are adequate to determine if the compounding assembly is operational, an alternative test may involve installing a test fixture where a transfer set is installed and having a known result indicated.

Figure 22:
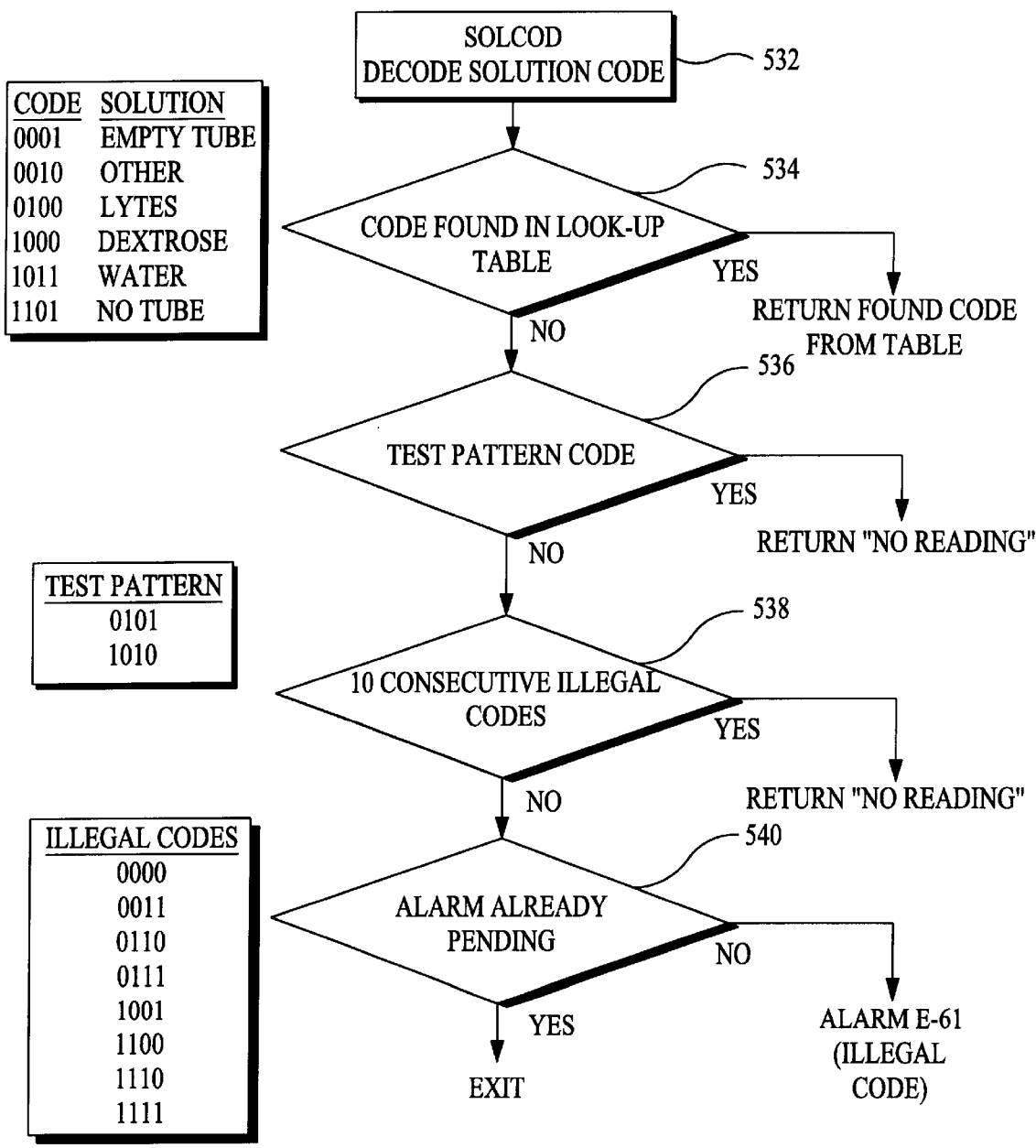

It is determined whether the test patterns are valid (block 326). In this regard, the sensing assembly 200 provides digital signals to the controller 48 on four lines. If any of these lines are shorted, false data can be transmitted. To check for such a condition, known test patterns consisting of 0101 and 1010 (as shown in FIG. 22) are sent from the sensor assembly 200 to the controller 48. If the test patterns fail, then an alarm is issued. In this regard, it should be understood that the controller 48 receives input signals from the various sensors, including the weight sensor 99 and the sensing assembly 200, and determines whether the conditions are satisfied to generate one of many preselected alarm signals. Such alarm signals result in alarm indications such as an audio alarm and visual alarms that appear on the display 78 and other locations as previously described. All of these events may be generally described as an alarm being issued.

It should be understood that the assembly includes alarm handling software logic for controlling the particular characteristics of the alarms that are generated. While the logic can be implemented in different ways, it is preferred that a look up table be used which controls the alarm characteristics, including the text shown on the display, whether LEDs are illuminated in a steady or flashing manner, whether a beeper or other type of audio alarm is sounded. Certain alarms will require the assembly to halt operation and wait for an operator to perform some task. Also, there is a correlation concerning the type of alarm that is generated and the type of operation that can be continued. Some alarm conditions will permit a bag to be completed, while others will require that the bag be discarded. The flow charts relating to the alarm logic will be hereinafter discussed in connection with FIGS. 26, 27A, 27B, 28A and 28B.

If the test patterns are valid, then weights corresponding to the desired volume of fluids to be transferred are calculated (block 328). After weights are calculated, the assembly begins to pump all stations (block 330) and motor usage alarm checks are made (block 332), which if unsuccessful, provide either an incorrect motor turn alarm or motor failed to turn alarm. If the motor checks are okay, then the bag is compounded and the total delivered amount is reported (block 334) resulting in a signal complete (block 336) if successful or an over delivery or under delivery alarm if not. With regard to the reporting function, when the bag is completed, the volume of each component actually transferred to the bag is preferably uploaded to a central computer for record keeping purposes, and also for billing purposes.

Figure 12:
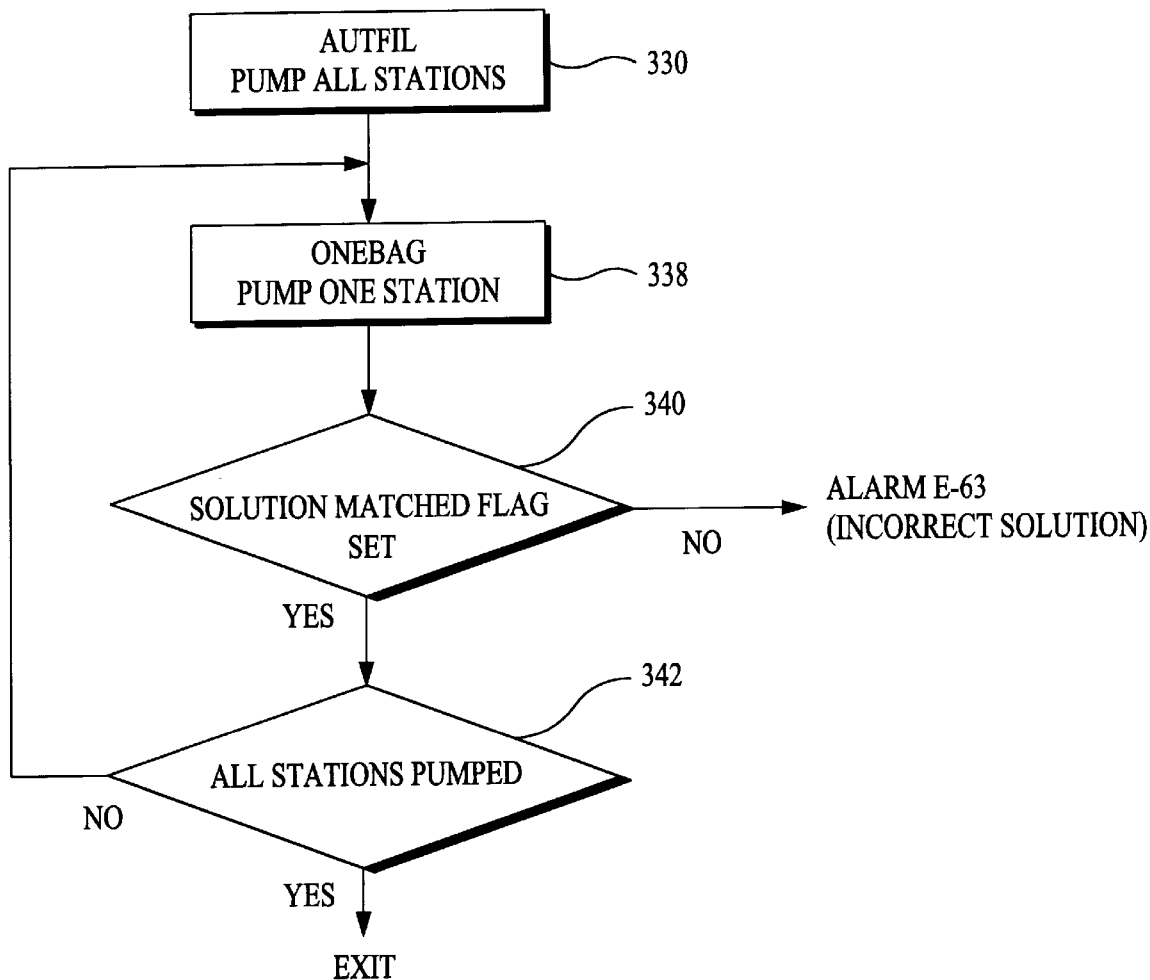

The pump all stations routine (block 330) is also shown in FIG. 12 to comprise a flow chart that begins by pumping a single station (block 338) until the correct amount of solution from the station has been pumped (block 340). If the solution pumped is detected as being incorrect, an alarm is sounded. If it is correct, then the next station is pumped (block 342) and when all stations are pumped, the routine is exited.

Figure 13:
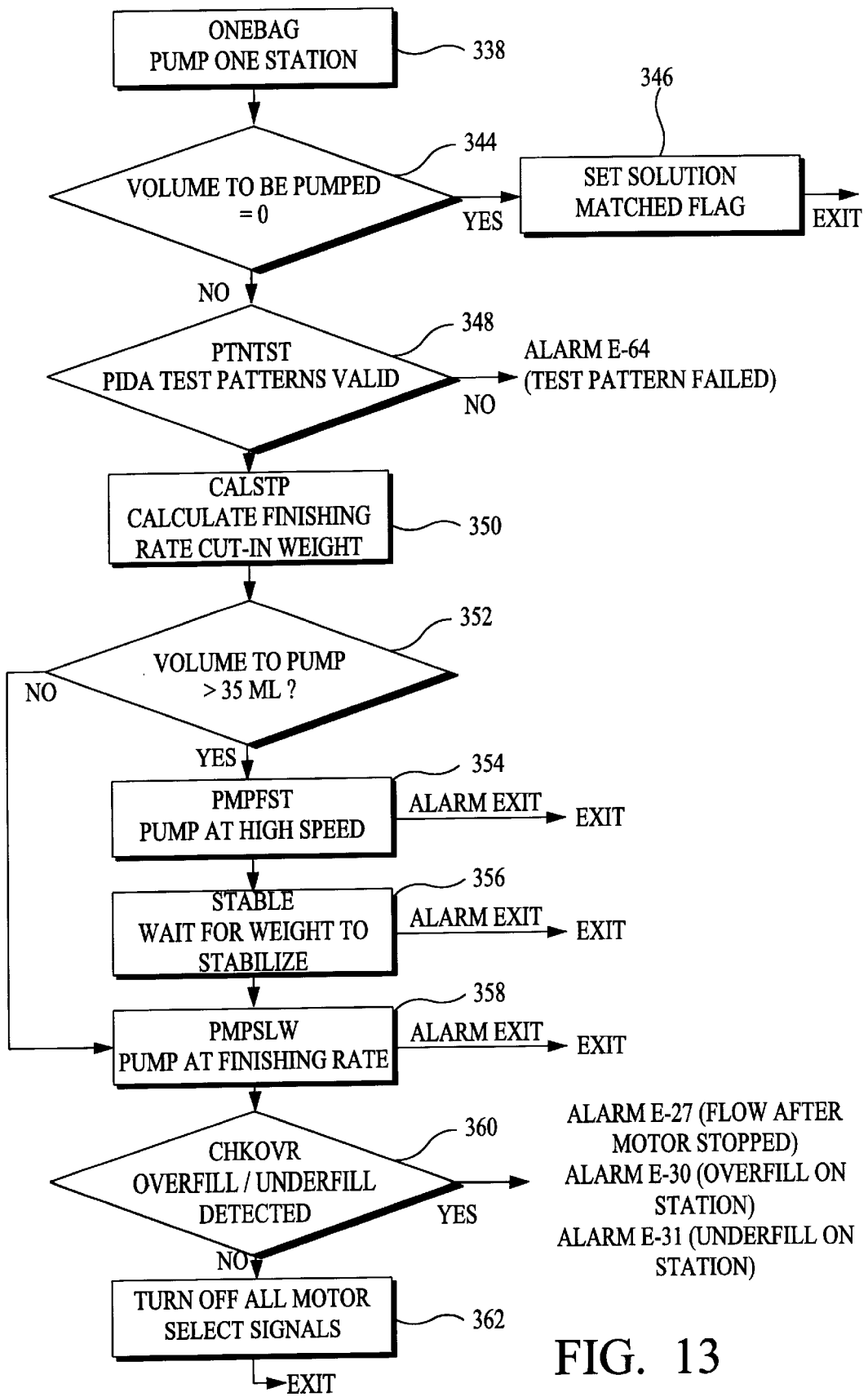

The pump one station routine is shown in FIG. 13 and begins by determining the volume to be pumped. Even if the volume to be pumped is zero (block 344), a solution matched flag is set (block 346) to insure that a correct solution is seen as a further check. If it is not zero, then test pattern checks are run (block 348). If the test patterns are valid, the assembly calculates the finishing rate cut-in weight (block 350), determines whether the cut in weight corresponds to a volume that is greater than 35 milliliters (block 352). If yes, pumping at high speed is carried out (block 354) up to the volume corresponding to the cut in weight, followed by a wait for the weight cell to stabilize (block 356) before pumping at a finishing rate (block 358) which is at a low speed to complete the addition of the corresponding source component. The controller determines whether there was an overfill or underfill (block 360) which results in an alarm indication if either an overfill or underfill occurred or if there is flow determined after the motor has stopped. This would occur for a free flowing condition where the weight sensor 99 detects an increase in weight of the receiving container even though the motor of that station had been stopped. If there is no overfill or underfill detected, then the motor select signals are turned off (block 362) and the routine is exited.

With regard to the motor select signals, it should be understood that each motor has two switches that must be closed for the motor to run. A main power switch to the motors must be closed, as must a motor select switch for each of the motors. If the assembly is in an idle mode where a user can input data, such as volume or specific gravity of source solution information, or if there is a device type alarm or flow type alarm, the controller opens all motors, select switchers and opens the main power switch. In this manner, the possibility that a single point failure mode existing which would inadvertently cause a motor to run is quite minimal. Thus, if the main power switch failed in an on condition, the motor would still not operate because the motor select switch is still in the open position as set by the controller. The final step of the routine of FIG. 13 is to turn off all motor select signals any time a receiving container has been completely filled or overfilled or underfilled sufficiently to create an alarm indication to that effect.

Figure 14:
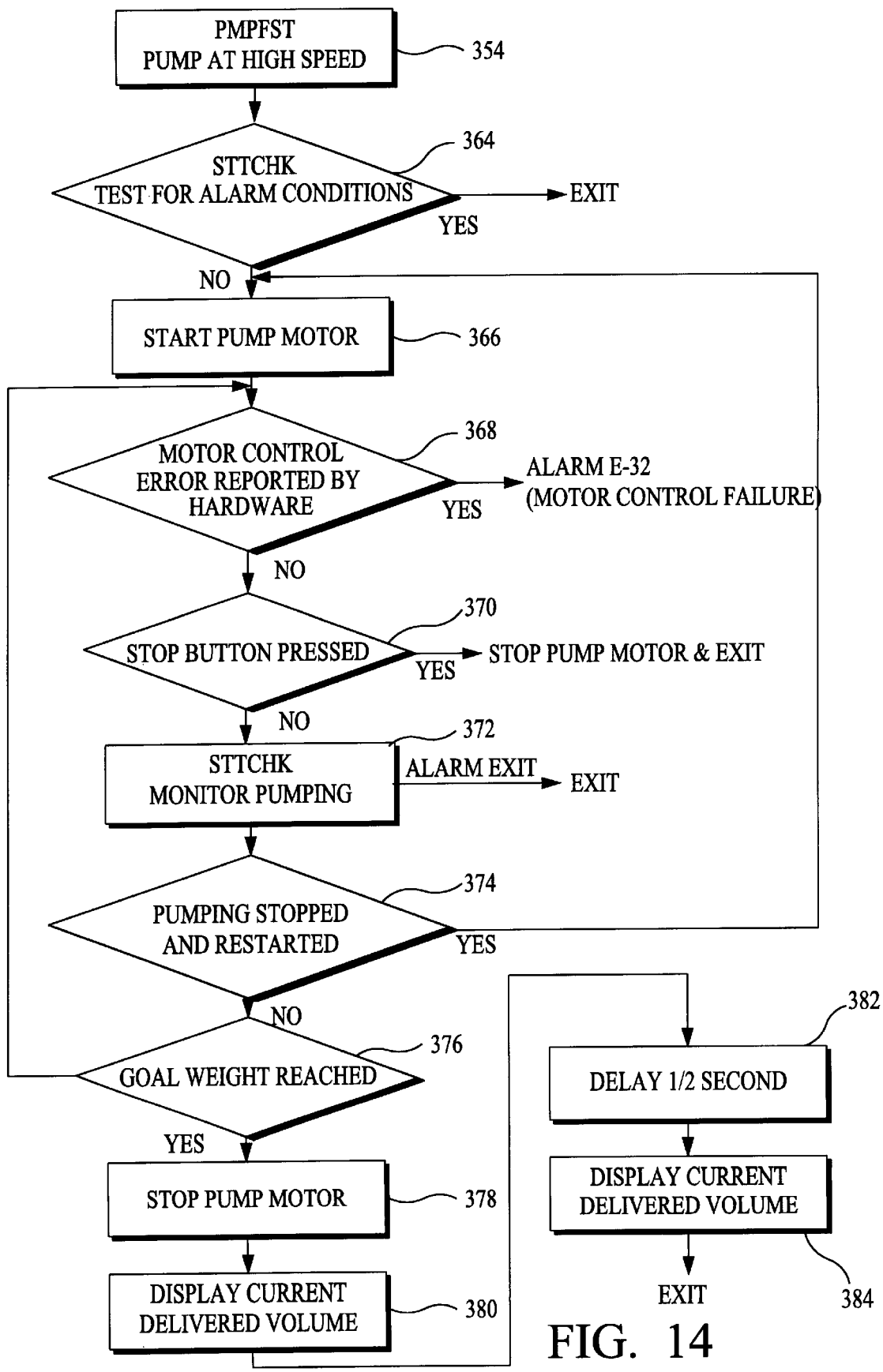

There is a routine for controlling the pump at high speed operation and referring to FIG. 14, the controller first tests for alarm condition (block 364) which if an alarm condition occurs, results in exiting the subroutine. If there are no alarm conditions found, the pump motor is started (block 366) and a determination of whether a motor control error has been reported is carried out (block 368). If there is an error, a motor control failure alarm signal is generated. If not, the routine determines whether a stop button has been pressed (block 370) which results in the motor stopping. If not, the routine then does a monitor pumping analysis (block 372). The routine then inquires whether pumping had been stopped and restarted (block 374) which if such had occurred, returns to the start pump motor step (block 366). If there was no pumping stopped and restarted, the routine determines if the goal weight had been reached (block 376), and if not, results in a return to block 368. If the goal weight has been reached, the pump motor is stopped (block 378). The delivered volume is displayed (block 380), a delay occurs (block 382) to allow the load cell circuitry to update the volume delivered and the updated delivered volume is again displayed (block 384), which ends the subroutine.

Figure 15:
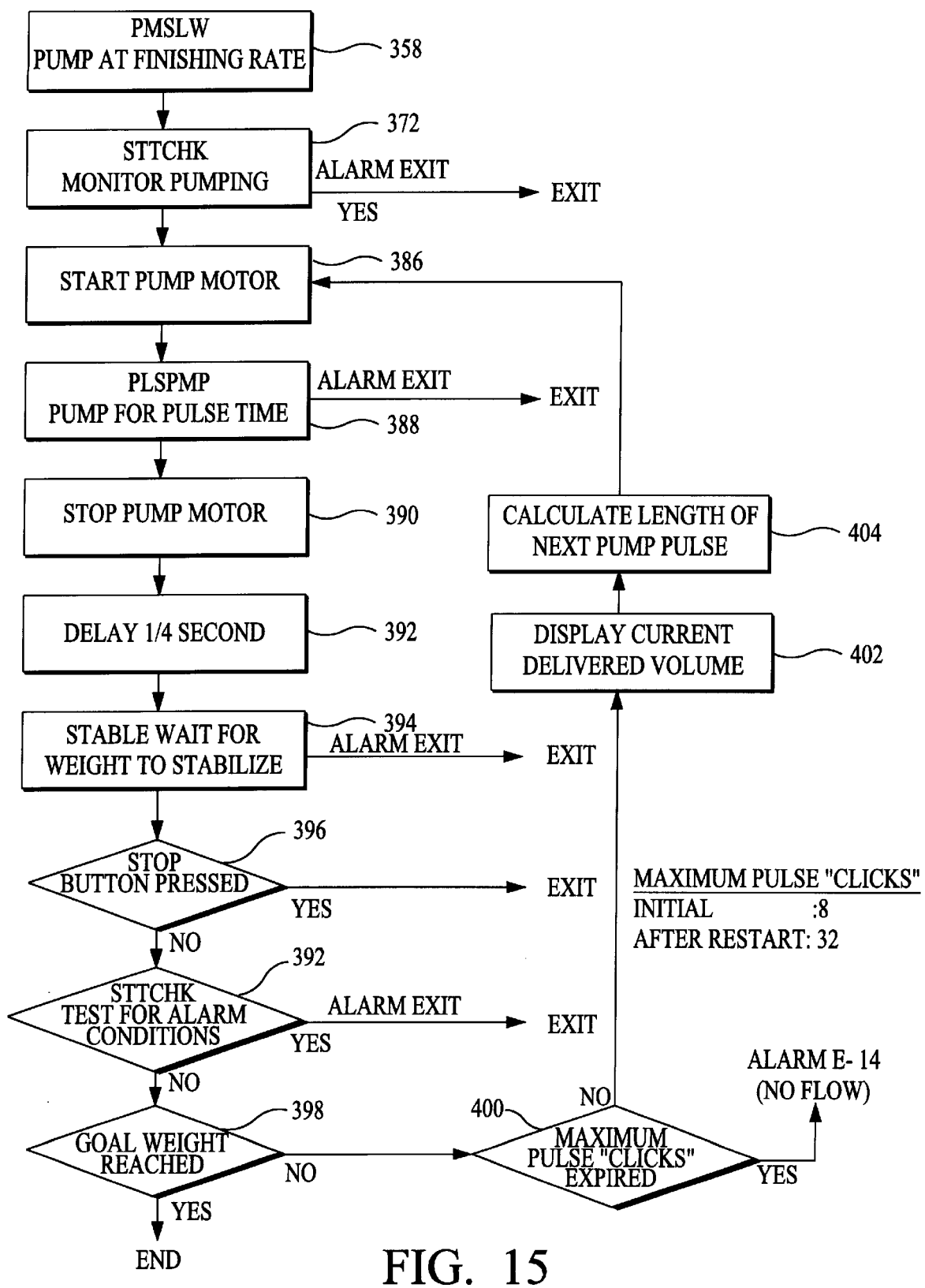

There is a separate subroutine for operating the pump motor at the slower or finishing rate and referring to FIG. 15, the initial command to pump finishing rate (block 358) results in a monitor pumping (block 372). If no alarm condition is detected, the pump motor is started (block 386) and results in the pump running for a predetermined pulse time (block 388) before the pump motor is stopped (block 390). At this point, there is a short delay (block 392) which is needed to stabilize the weight (block 394). The subroutine inquires whether the STOP button has been pressed (block 396) which if so, results in exiting of the routine. If not, a further check for alarm conditions is run (block 372). If no alarm conditions are present, the subroutine inquires whether the goal weight has been reached (block 398) and if so, ends the subroutine. If it has not been reached, then the subroutine determines whether the maximum number of motor drive pulses or clicks have expired (block 400), which may initially be 8 pulses or 32 pulses after a restart. If the maximum number of pulses have not expired, the subroutine displays the current delivered volume (block 402) and calculates the length of the next pump pulse (block 404) before it again starts the motor (block 386). If the maximum number of pulses have expired (block 400), then a no flow alarm signal is generated.

In accordance with yet another important aspect of the present invention, it is important that a completed compounding process produce a bag having the proper composition and that it continue to be monitored after completion of the filling of the bag to the prescribed amount after the pumps have been shut off. It is known that there can be some running of fluid from a source bag to the receiving bag even after the pumps have been shut off if there is less than complete sealing in the peristaltic pump operation. Therefore, a continuation of monitoring of the weight of the receiving bag by the sensor 99 is done after the compounding has been completed. This is done by monitoring the weight sensor to determine that no fluid continues to flow into the receiving container prior to the operator sealing the transfer tubing and removing the receiving container from the load cell 100. If the continued free flow is monitored, then a free flow alarm signal is generated by the controller and is displayed. The process is set forth in the subroutine shown in FIG. 16.

Figure 25:
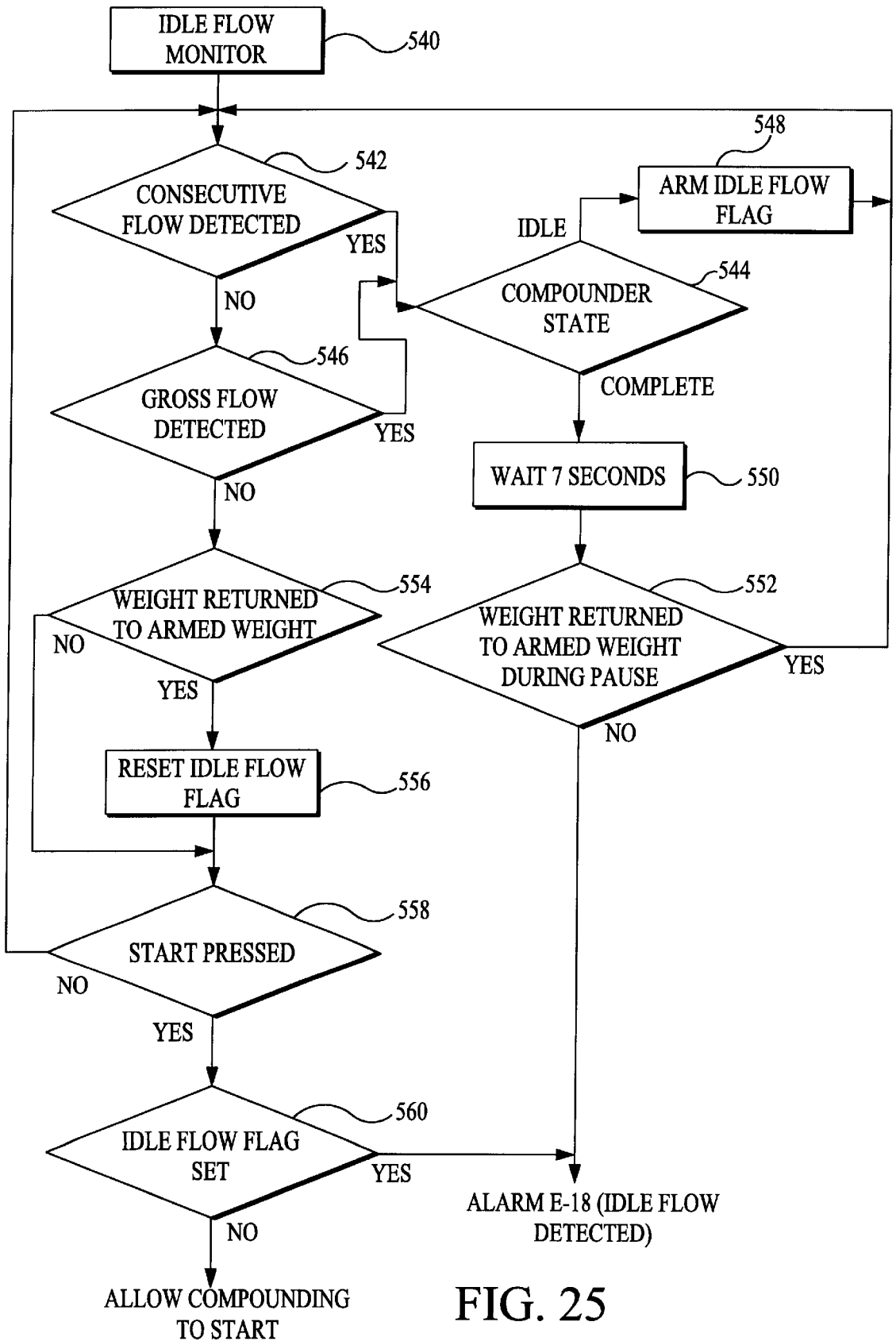

Once the check is invoked (block 360), the controller determines whether the amount of fluid delivered, as determined by the weight from the weight sensor 99 which senses the receiving container and its contents, is greater than or equal to the goal weight plus some tolerance value (block 406). If it is greater than or equal to the goal weight and tolerance, then an overfill alarm signal is generated, but if not, then the routine causes the delivered amount to be measured to determine if it is less than or equal to the goal amount minus a tolerance value (block 408). If so, the controller generates an underfill alarm signal. If the amount delivered is greater than the goal minus the tolerance, then the routine delays for about ½ second (block 410) and determines whether the weight increased by some predetermined amount, such as at least 4 grams (block 412), which if so, results in a flow after motor stop alarm. If no weight of at least 4 grams is detected, then the subroutine is exited. This flow after motor stop determination is made once after the motor stops. Another similar flow check will be hereinafter described in connection with FIG. 25.

Figure 17:
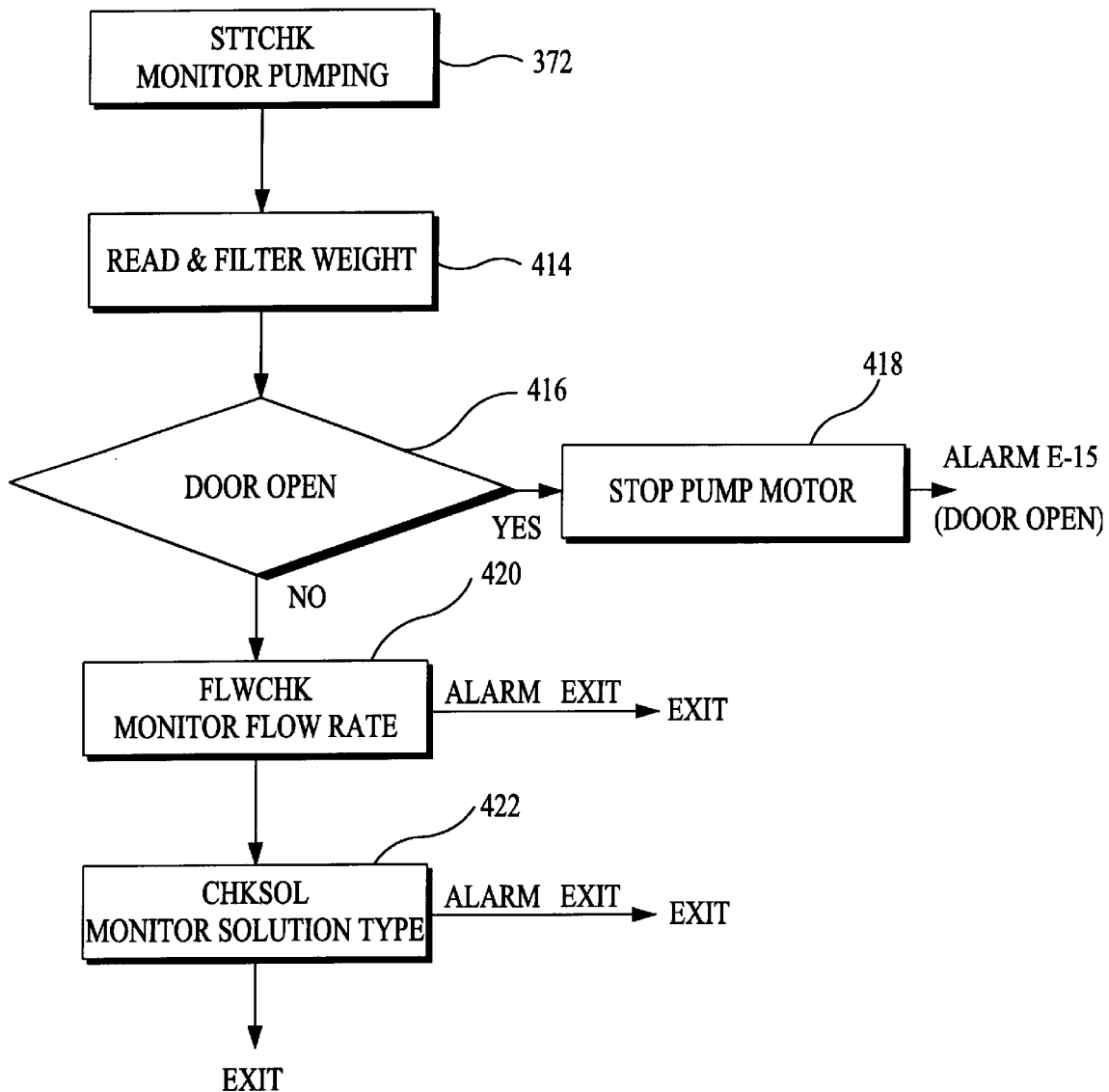

The monitor pumping portion of the routine shown in FIG. 14 (block 372) further comprises a subroutine shown in FIG. 17 which results in the weight being read (block 414), and the controller determining whether the door to either of the housing 38a or 38b or sensor 200 (FIG. 1) is open (block 416). If any of the doors are open, the pump motor is stopped (block 418) and an alarm signal generated. If any of the doors are not opened, the flow rate is monitored (block 420) and the solution type is determined (block 422) before the routine is exited.

Figure 18:
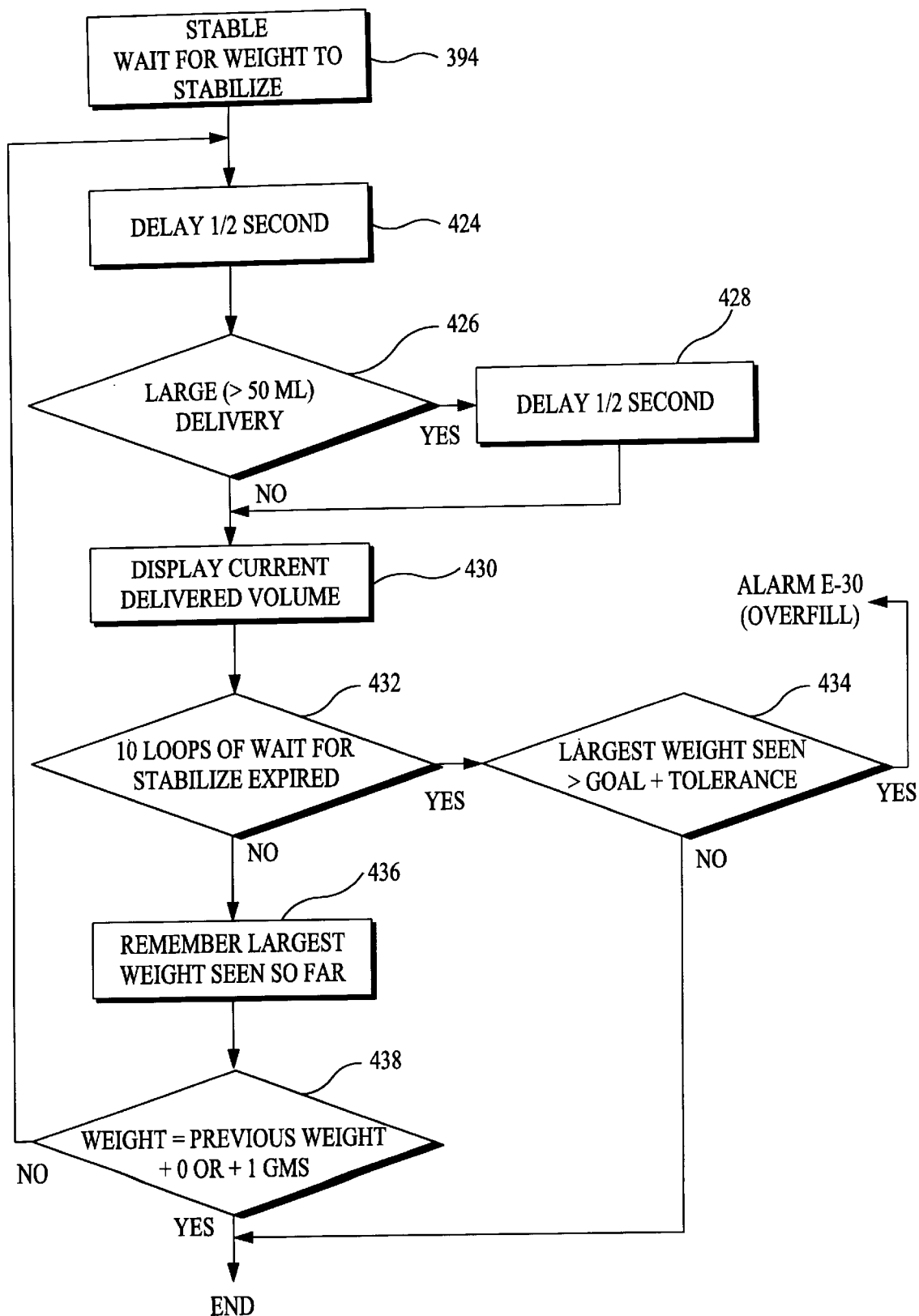

There is a subroutine for the controller to run when the step of waiting for weight to stabilizes called (block 394) and this is shown in FIG. 18 and includes a delay of approximately ½ second (block 424) for the controller determines whether there has been more than 50 milliliters programmed (block 426) which if so, results in another approximately ½ second delay (block 428). If the programmed volume is less than 50 milliliters or the ½ second delay has expired, the subroutine calls for the delivered volume to be displayed (block 430) and then up to ten loops of waiting are run (block 432). If the largest weight measured is greater than the goal weight plus some tolerance (block 434), then an overfill alarm signal is generated. However, if it is less than the goal plus tolerance, the subroutine is ended. If the ten loops of delay have not expired, the subroutine stores the largest weight that has been measured (block 436) and compares that weight to determine if it is equal to the previous weight plus some marginal tolerance (block 438). If the weight is not equal to the previous weight plus some tolerance, the subroutine returns to block 424. If it is equal to the previous weight plus some amount, then the subroutine is ended.

Figure 19:
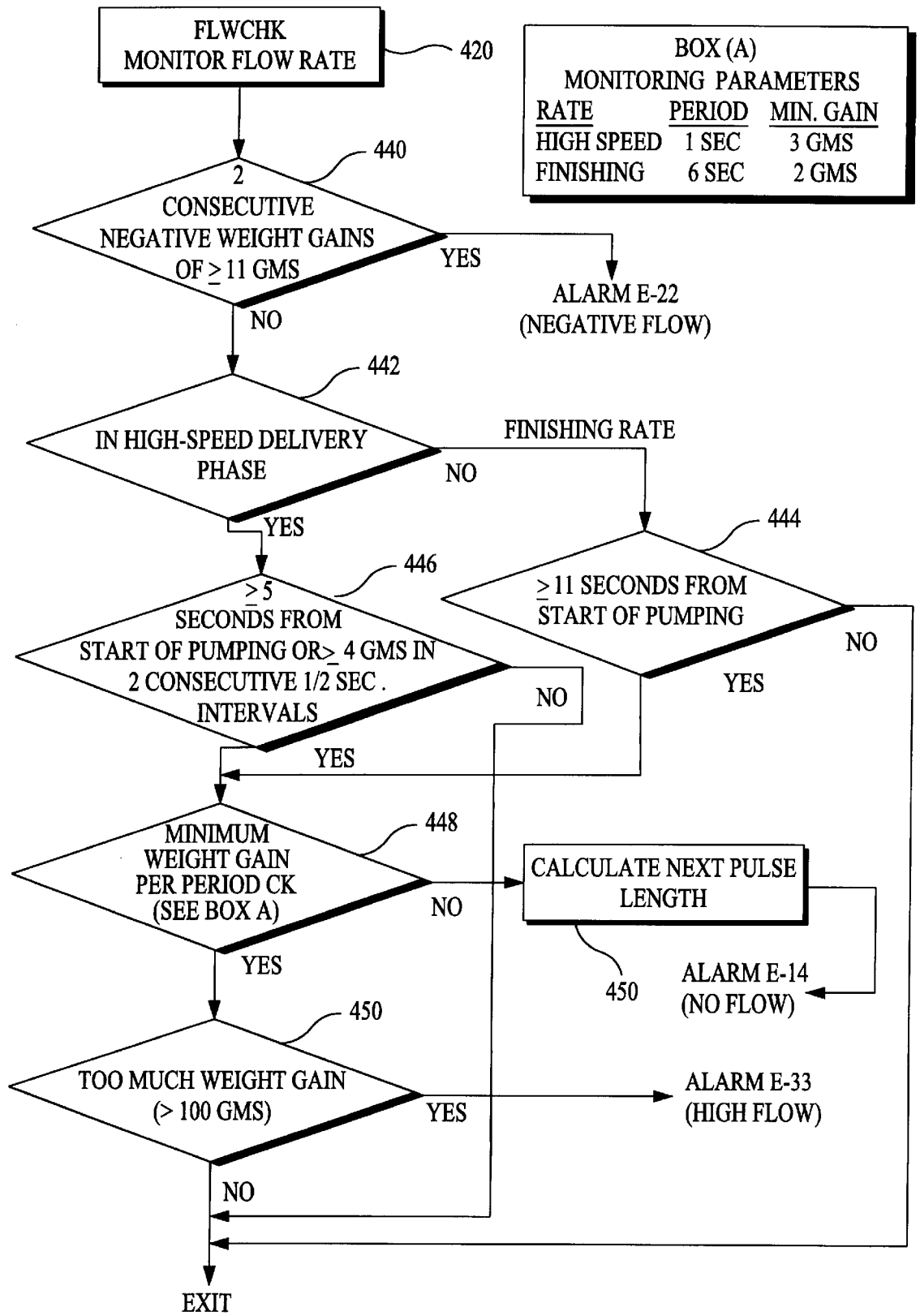

The controller also has a subroutine for performing the monitor flow rate check (block 420) which is shown in FIG. 19 and it is adapted to determine if a negative flow condition, no flow condition or high flow condition occurs. The subroutine initially determines whether two consecutive negative weight gains greater than 11 grams have occurred (block 440), which if such has occurred, results in a negative flow alarm. If not, the subroutine determines whether the pump was operating at high speed (block 442). If it is not operating at high speed, the software inquires whether it has been running at least 11 seconds from the beginning of pumping (block 444), and if not, results in exiting of the subroutine. If the motor is in high speed operation, then it determines if it has been at least five seconds from start of pumping or at least 4 grams of weight gain has occurred in consecutive ½ second intervals (block 446), which if so, results in an inquiry being made whether the minimum weight gain for this period has been achieved (block 448). If not, it calculates the next pulse length before driving the pump motor (block 450) and issues a no flow alarm signal. If the minimum weight gain has been achieved, then it inquires as to whether there has been too much weight gain, i.e., a weight gain in excess of 100 grams, which if such occurred (block 451), results in a high flow alarm signal being generated. If the weight gain is not too much, the subroutine is exited.

As will be described, an alarm condition is generally issued when the sensed characteristic does not match the characteristic of the solution which has been input as the correct solution. However, it is desired to further distinguish if the sensed characteristic does not conform to the correct characteristic due to the incorrect solution in the transfer tube or to the correct solution being in the transfer tube and another condition occurring which generates the different sensed characteristic. This is important as required corrective actions to an incorrect solution indication may be more involved than those required corrective actions for other conditions which also give rise to different sensed characteristics.

By way of example, it may be desired to require a flushing of the transfer tube and disposal of the final mixing container if an incorrect solution alarm is generated, whereas an alarm generated by depletion of a source container may only require the attachment of a new solution container without a required flushing or disposal. A no flow alarm may also be generated by such occurrences as a kink in the transfer set tubing as well as an empty source container.

Thus, in accordance with yet another important aspect of the present invention, it has been found that a false incorrect solution alarm signal can be generated when the pump motor is operating at high pumping rates and a source container is exhausted due to the fact that there is partially empty tubing or conduits which can produce readings by the sensor assembly 200 that an incorrect solution is present. In accordance with the present invention, an incorrect solution alarm signal is only generated if 10 consecutive solution mismatch determinations are detected. If an empty tube reading occurs, the controller of the present invention uses that empty tube reading to reset the incorrect solution consecutive mismatch counter. Since the exhausted source container condition is typically accompanied by empty tube readings in addition to incorrect solution readings, the realization of the combination of these conditions thereby eliminates the majority of false incorrect solution alarm signals that could otherwise occur under these conditions. It should be understood that the mismatch counter reset does not apply when operating in the finishing or low speed pumping rate. In addition, it is preferred that in the consideration of being able to differentiate no flow from incorrect solution, it is preferred that the weight gain, i.e., flow of fluid into the receiving container be checked in three consecutive ½ second intervals. If any of the three ½ second period intervals shows low flow, i.e., less than about 3 grams, then a no flow condition is indicated rather than a false incorrect solution alarm. This aspect of the present invention is carried out by the controller in accordance with the flowcharts shown in FIGS. 20, 21 and 23.

In accordance with still another important aspect of the present invention, the assembly is designed so that when a source bag 16 runs out of fluid, a no flow alarm indication should occur. However, nonvented collapsible containers run out of fluid, the system may generate an incorrect solution alarm signal rather than a no flow alarm. The cause of the discrepancy is believed to be due to partial solution segments remaining in the transfer set tubing near the sensing assembly 200. The preferred embodiment of the present invention utilizes load cell 100 data in conjunction with the sensor assembly data to determine if the mismatch between the sensed solution and PID solution is due to a no flow condition instead of the wrong solution in the transfer tube prior to generating an incorrect solution alarm signal. This determination of a no flow is generally accomplished by monitoring the rate of weight change and determining that the weight change is less than expected for a standard pumping sequence. The system therefore generates a no flow alarm signal before it generates an incorrect solution alarm signal. In this regard, it is preferred that the system wait approximately 3 seconds before it determines any weight change after a pump motor has initiated operation.

Figures 2, 20:
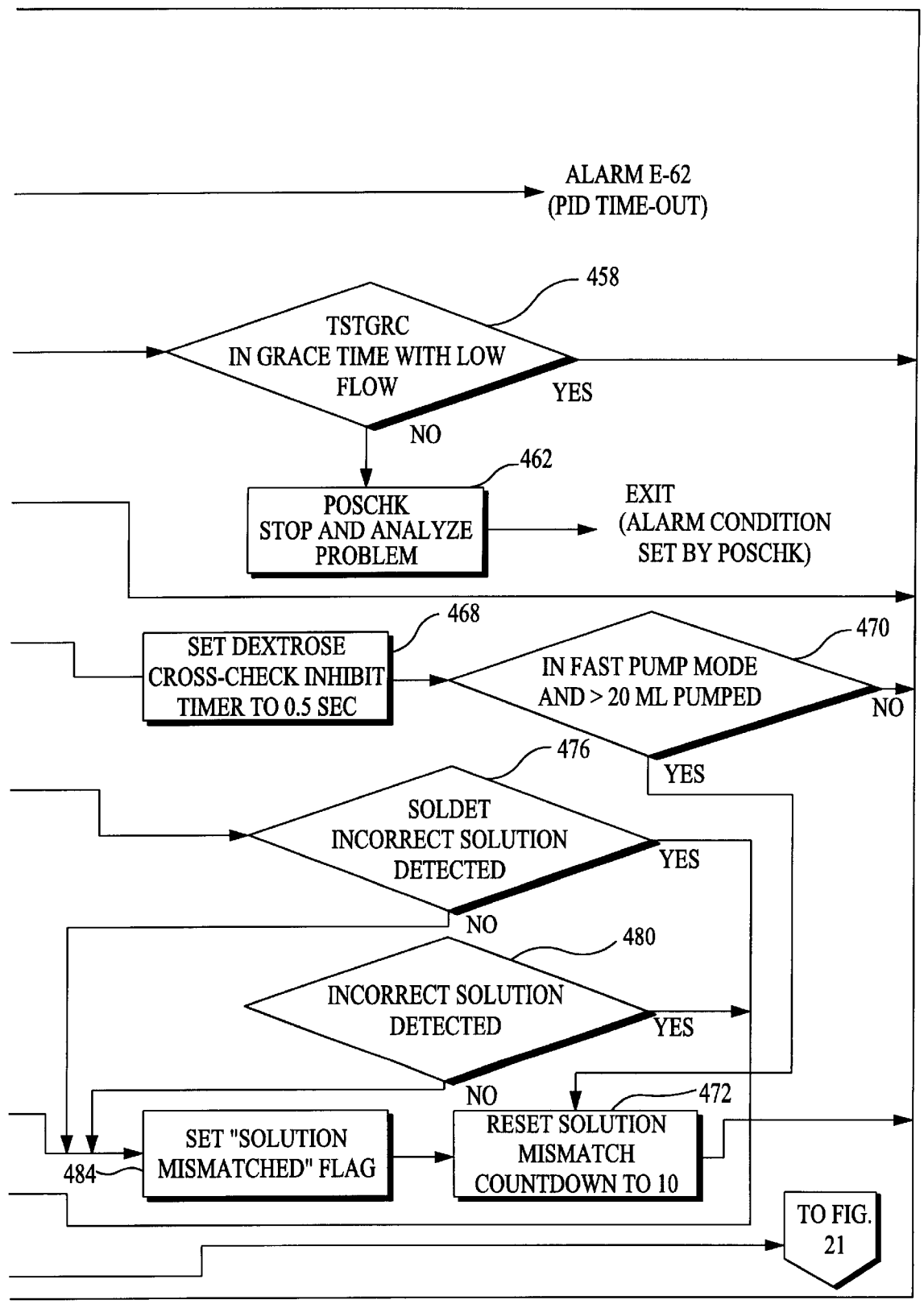
Figure 21:
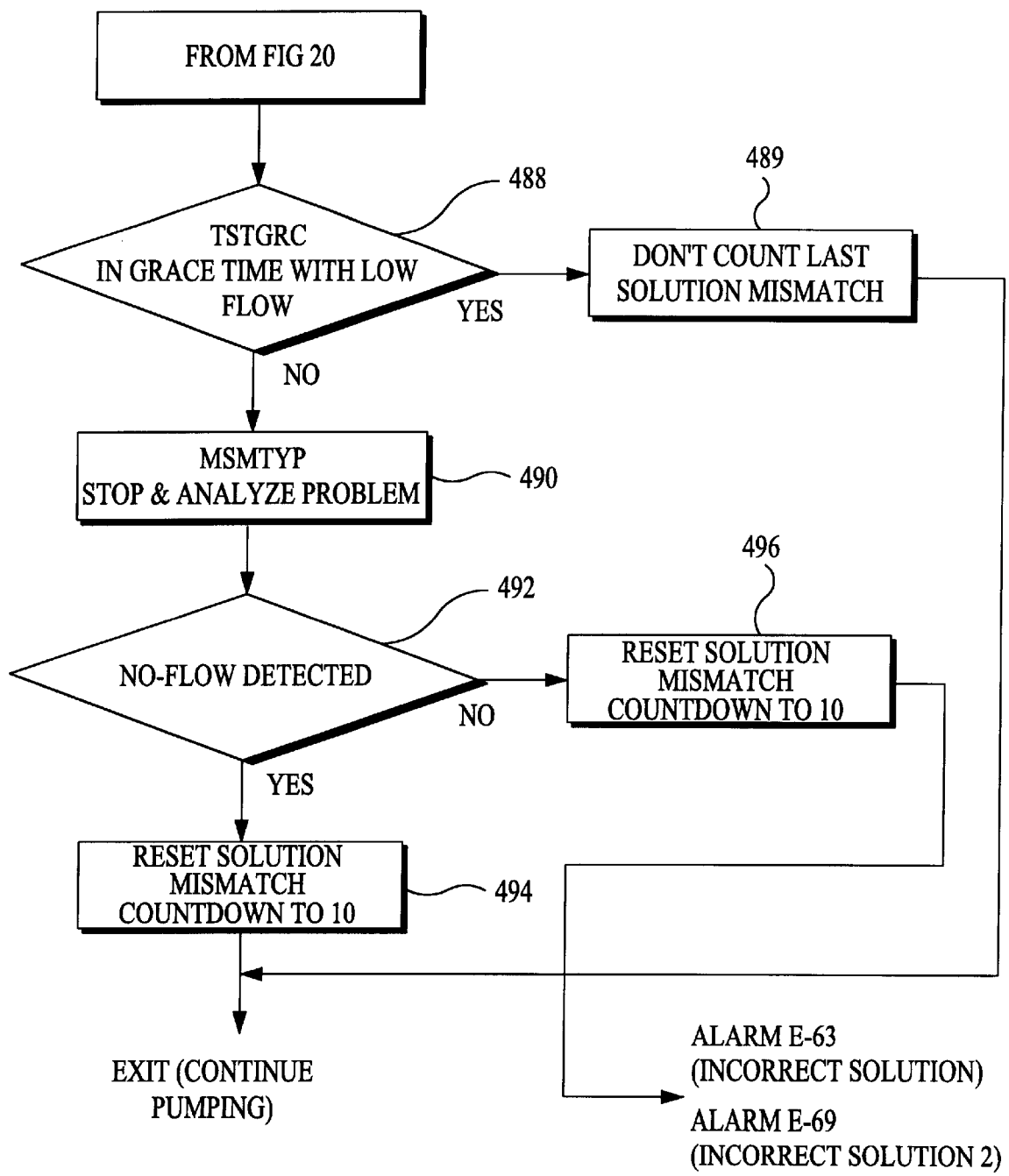

More particularly, with respect to the determination of the type of solution that is sensed by the assembly 200, and referring to FIGS. 20 and 21, the subroutine begins by determining whether the pump motor is operating at a fast speed (block 452) or is between pulses in slow speed operation. If the answer is no, the subroutine is exited, which means that pumping is continued. If yes, the subroutine waits for the positive ID reading from the sensor 200 (FIG. 1) which indicates that the sensed solution corresponds to the inputted solution and executes a time out decision (block 454). If no reading was received within the approximately 1 second time out period, then a time out alarm signal is generated. If it has not timed out, then the routine inquires to determine if there have been 10 consecutive illegal solution codes (block 456). If 10 illegal codes have been received, the routine then determines if a low flow condition existed within the time out period (block 458) and if so, exits the routine. If not, the subroutine stops and attempts to analyze the problem (block 462) and generates an alarm condition. If there have not been 10 illegal codes received (block 456), the software determines whether a no reading condition has occurred (block 464), which if yes, results in the subroutine being exited. If no, it inquires whether there has been an empty tube reading made (block 466). If so, a dextrose cross check inhibit timer is set at approximately ½ second (block 468) and an inquiry is made whether the pump is operating in the fast speed mode and greater than 20 milliliters has been pumped (block 470). If no, the subroutine is exited, but if so, a solution mismatch count down to 10 is reset (block 472) and the routine is exited. The inhibit timer is set because if there is an empty tube, no fluid is going into the bag, so there is no need to monitor the flow rate.

If there has not been an empty tube reading (block 466), that means there is fluid in the tube and the flow rate can be measured, which inherently takes some time to accomplish because the flow rate history is implicated. The subroutine then determines whether the solution is dextrose (block 474) which if so, results in an incorrect solution check being made (block 476). If the solution is not dextrose, then the subroutine determines whether the solution is water (block 478) and inquires whether the solution is incorrect (block 480) which if not, results in setting the solution matched flag (block 484) If the solution is not dextrose or water, a determination is then made as to whether the programmed solution matches the positive identification ("PID") reading (block 482). If it does, the solution matched flag is produced (block 484) which resets the solution mismatch countdown to 10 (block 472) and results in an exit of the subroutine. If the solution does not match the PID reading, the subroutine determines if there are 10 consecutive solution mismatches (block 486) which if not, results in exiting of the subroutine. If the answers to the inquires in blocks 476, 480 and 486 are yes, then the subroutine continues to FIG. 21. It should be noted that a yes from either of blocks 476 or 480 count as one of the 10 solution mismatches in block 486.

If the correct solution occurred within the grace time and with a low flow indication (block 488), then the subroutine does not count the last solution mismatch (block 489) and exits the subroutine, i.e., it continues pumping. The rationale for this is that if the sensing assembly 200 is not seeing the right solution and if the minimum flow criteria is not being met, a solution mismatch alarm is not triggered, and the last mismatch is not counted until fluid flow is detected. The alarm therefore will not be triggered until fluid flow is measured.

If the incorrect solution was not detected within the grace time with a no flow condition, then the routine again stops and attempts to analyze the problem (block 490) and then determines whether a no flow condition exists (block 492). If yes, the mismatch countdown is again reset to 10 (block 494) and the subroutine is exited. However, if a no flow condition was not detected, a mismatch countdown is again reset to 10 (block 496) and an incorrect solution alarm signal is generated.

Figure 24:
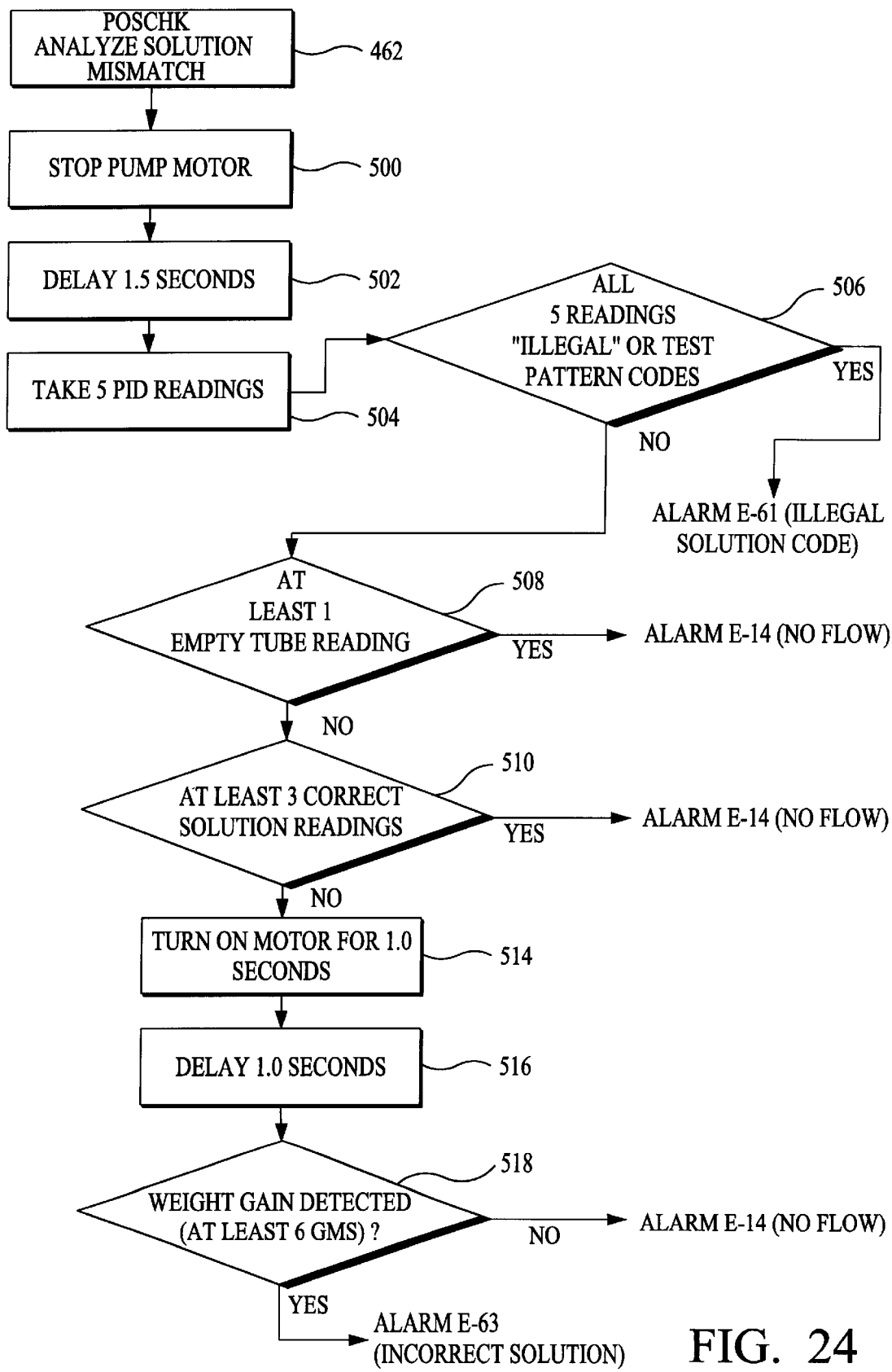

When the subroutine of FIG. 20 operates and reaches the stop and analyze problem (block 462), it initiates a subroutine shown in FIG. 24 which initially performs a determination as to whether at least 8 of the last 10 PID readings are empty tube readings or not (block 498). This determination is performed because it has been found that under certain situations when a certain solution is being pumped, it can be combined with air, and can result in an empty tube indication. This determination effectively insures that such a false empty tube indication and consequent incorrect "install" alarm does not occur. If at least 8 of the last 10 readings are empty tube readings, it generates an "install" alarm to alert the user that the transfer set may not be installed correctly. If there are less than eight empty tube readings, the subroutine stops the pump motor (block 500), delays for 1½ seconds (block 502), takes five PID readings (block 504) and then determines if the last 15 PID readings are illegal or test pattern code readings (block 506), which if yes, results in an illegal solution alarm signal being generated.

The last 15 PID readings are considered because of a special circumstance that could occur as a result of stopping the motor and delaying 1.5 seconds. Because of the delay and the stopped motor, examining a lesser number of readings, such as 5 PID readings, for example, could easily result in an incorrect solution alarm being generated. By using 15 of such readings, the possibility of an false incorrect solution alarm being generated is greatly diminished. With regard to the 1½ second delay, this permits the boundary between any solution and air that may be present in the sensing assembly 200 to settle down, essentially letting gravity influence the flow of fluid through the assembly 200. This phenomenon has been experienced and the delay largely eliminates the problem.

If the last 15 PID readings are not illegal or test pattern codes, the subroutine inquires whether there was at least one empty tube reading (block 508) which if so, results in a no flow alarm signal being generated. If not, the subroutine determines whether there were at least three correct solution readings (block 510), which if yes, results in a no flow alarm signal being generated. However, if the determination was no, the subroutine determines if the station is actually programmed for pumping electrolytes (lytes)(block 512), and also determines if there are any missing tube or electrolytes readings (block 513). If there are, a no flow alarm is generated, but if not, the subroutine determines if there were an dextrose or water detected in the last 15 PID readings (block 514). If there were, a no flow alarm is generated, but if not the pump motor is turned on for 1 second (block 515). A no determination that electrolytes are not being pumped (block 512) also results in the motor being turned on for approximately one second (block 515), a delay is run (block 516) and a determination is made whether a weight gain of at least 6 grams was detected (block 518). If not, a no flow alarm signal is generated and if yes, an incorrect solution alarm signal is generated. The logic contained in blocks 512, 513 and 514 is used to avoid the situation where electrolytes are being pumped and air is in the solution, which often had resulted in an incorrect solution alarm being generated. However, the logic of blocks 512, 513 and 514 largely eliminates this possibility.

Figure 23:
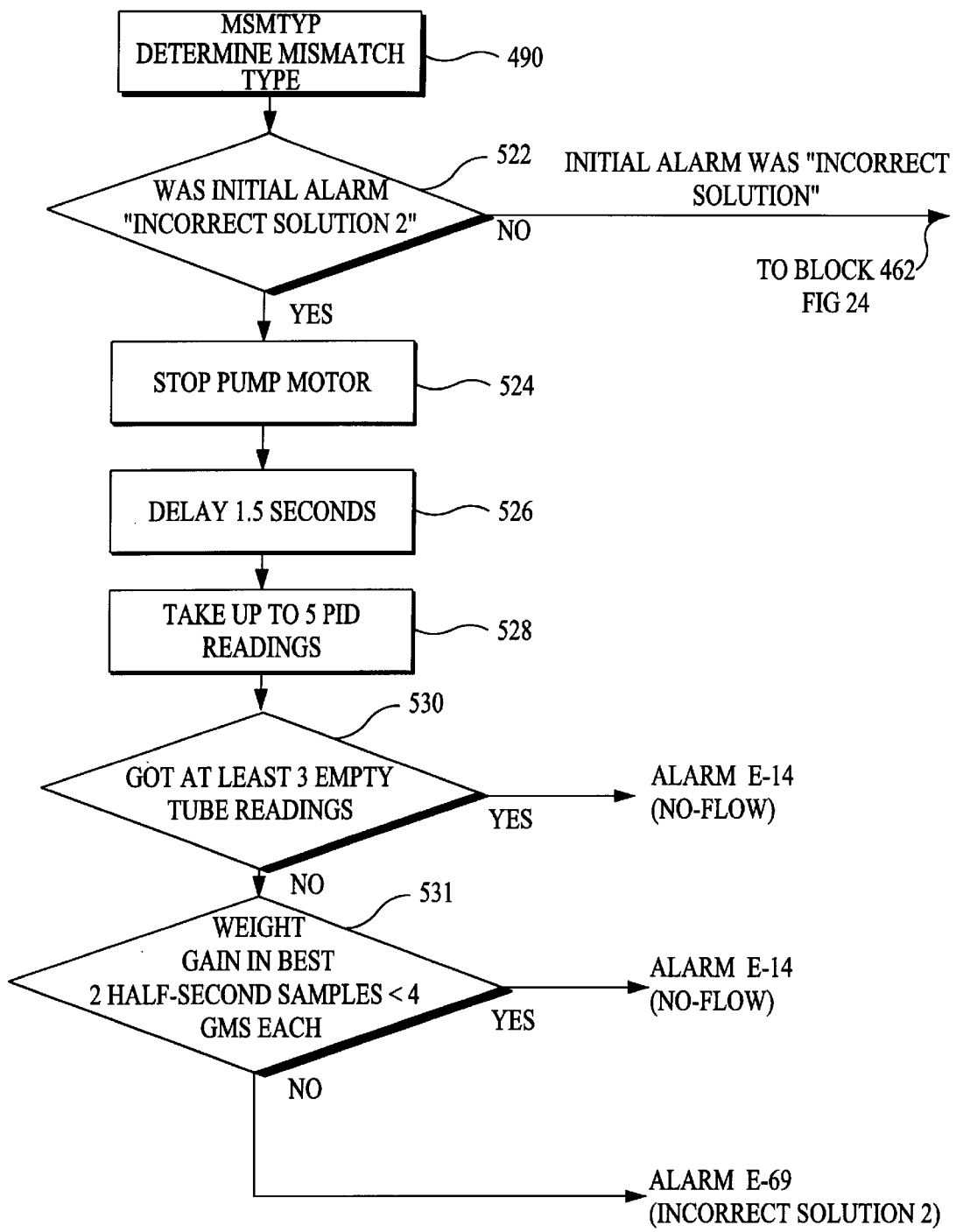

In a similar subroutine, the stop and analyze problem (block 490) of FIG. 21 also comprises a subroutine shown in FIG. 23 for determining the mismatch type (block 490). The software initially determines whether an incorrect solution alarm condition was initially detected (block 522). If not, the subroutine passes to block 462 in FIG. 24, but if yes, results in the motor being stopped (block 524), a 1.5 second delay being run (block 526), and the acquisition of five additional PID readings (block 528), a determination as to whether at least three of the readings were empty tube readings (block 530). If not, the routine determines if there had been a weight gain in last 2 half second samples that was less that 4 grams each (block 531). If yes, a no flow alarm is generated, and if no, an incorrect solution alarm signal is generated.

An example of the decoding of the solution code is carried out by a subroutine shown in FIG. 22 beginning with (block 532). The subroutine determines whether the code is present in a look up table (block 534) which if yes, returns the found code from the table and if not, performs a test pattern code inquiry (block 536) which may result in a no reading response. If not, it determines if there have been ten consecutive illegal codes received (block 538) which if not, results in a no reading indication. If 10 illegal codes have been consecutively returned, the subroutine determines whether there is an alarm already pending (block 539) which if not, results in the illegal code alarm signal being generated and if yes, exits the subroutine.

Figure 16:
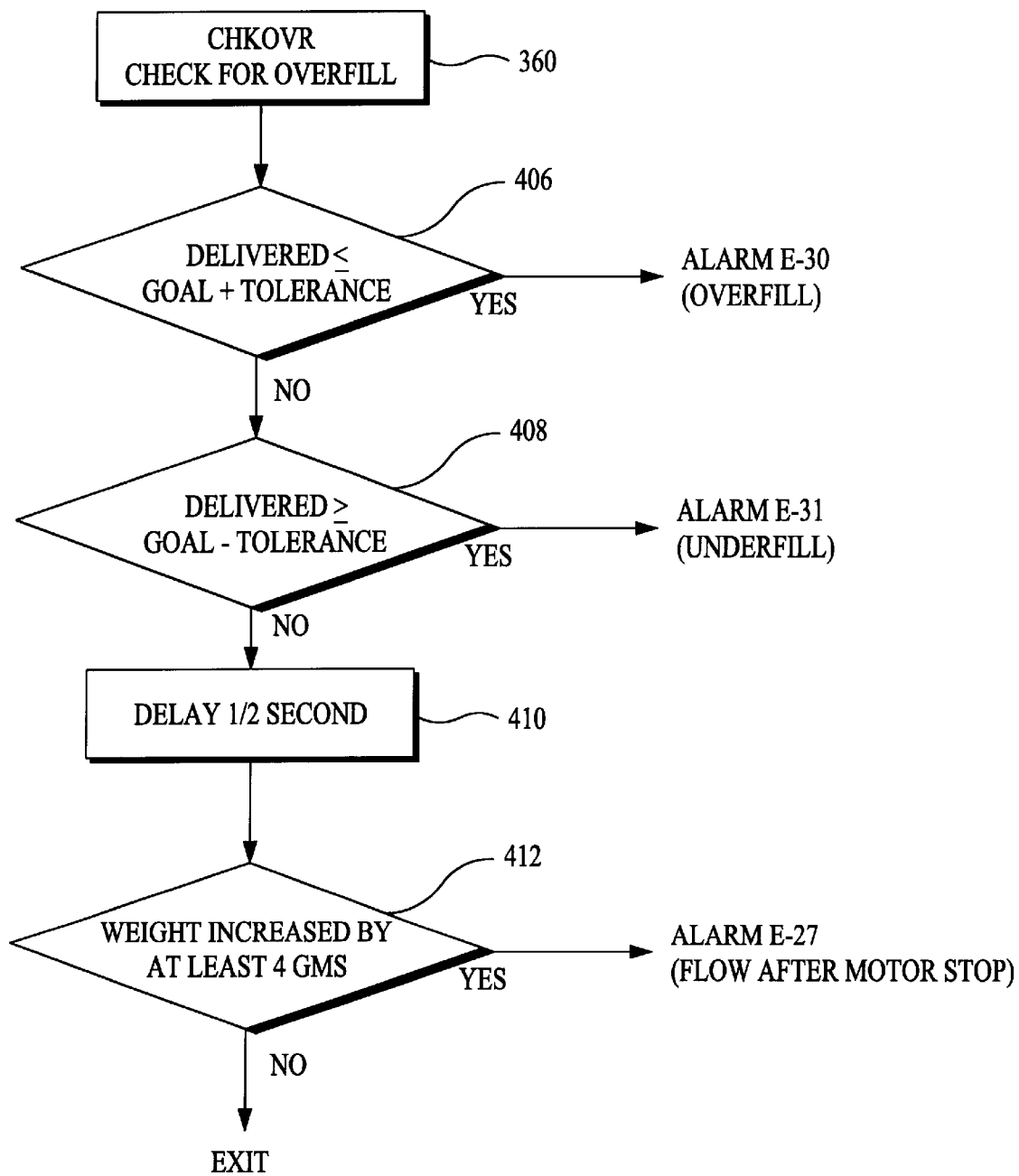

While the flow after motor stopped routine has been described in FIG. 16, that routine is only run once after the motor has been stopped. Another similar idle flow monitor is provided by the compounder assembly of the present invention and is shown in the flow chart of FIG. 25. The routine is started at 540 and initially determines if there are periods of time at which the same rate of flow occurs consecutively (block 542), with the same rate being within 6.25% of a previous measurement. If such consecutive flow is detected, the compounder determines whether it is in an idle state (block 544) or the bag is complete. If the compounder is idle, and an empty bag is placed on the hook, it is apparent that the compounder assembly should not be started if a wait gain has been detected by the weight sensor 99. If it is in an idle state, then an alarm idle flow flag (block 548) is set which will produce an alarm if the start pushbutton is depressed and the situation has not been rectified. A different situation exists if the bag has been completed and idle flow detected. In this instance, the routine waits seven seconds from a weight gain detection (block 550) and then determines if the weight has returned to the armed weight after the pause (block 552). If the weight has been returned, then the program returns to block 542. If it has not returned, then an idle flow detected alarm is produced. The armed weight is that which exists after a gain has been detected, i.e., it is at the beginning of a period. If a one gram weight gain per minute is detected, then an idle flow alarm will be produced. The rationale for the seven second delay (block 550) is that after a bag has been completed, it is common practice for it to hang on the hook (as shown in FIG. 1) until a pharmacist comes by and initials or otherwise approves it for a patient. It has been found that the process of initialing the bag will jostle it and cause a weight change to be detected. The seven second delay enables such a practice to occur without creating an idle flow detection alarm. It should be understood that the amount of the delay can be somewhat smaller than seven seconds and can be appreciably longer, i.e., up to twenty seconds or more, if desired. The seven second delay is not triggered until after a weight gain is detected which means that the bag may remain on the hook for an extended time until a pharmacist or other technician would come by and jostle it.

The routine also has a gross flow detection step (block 546) which measures larger gains in weight over several seconds which may occur as a result of a pump motor remaining on or a tube not being properly installed on a rotor so that a large volume flow could occur. If such a gross flow is detected, then the compounder state determination is made as previously discussed (block 544). If no gross flow is detected, the routine determines whether weight has returned to the armed weight (block 554) which if so, results in the idle flow flag being reset (block 556), but if not, skips this step so that when the start button is pressed (block 558), a check is made as to whether the idle flow flag has been set (block 560) which if yes, results in the alarm being generated and if not, allows compounding to start.

In accordance with yet another aspect of the present invention, a problem has existed where an incorrect solution alarm signal can occur in situations where the correct solution is actually being pumped if the source container is emptied such that a no flow alarm signal occurs at a point near the ultimate receiving container volume, i.e., within approximately 5 milliliters of completion. If the pump is then restarted, then the goal rate may be reached by filling the bag with solution that is in the tubing between the sensor assembly 20 and the final receiving container without installing a new source container. The present invention allows a restart from a no flow alarm if the prescription is at a point near completion. In addition the invention may be configured to only allow completion if the correct solution and only empty tube values are reported by the sensor assembly 200 from the time that the pump is restarted, and the goal weight is then reached. In other words, the assembly may be configured to enable the bag to be completed when it is very close to completion and it is known that only the correct solution or empty tube reading occurred since restart.

Figure 26:
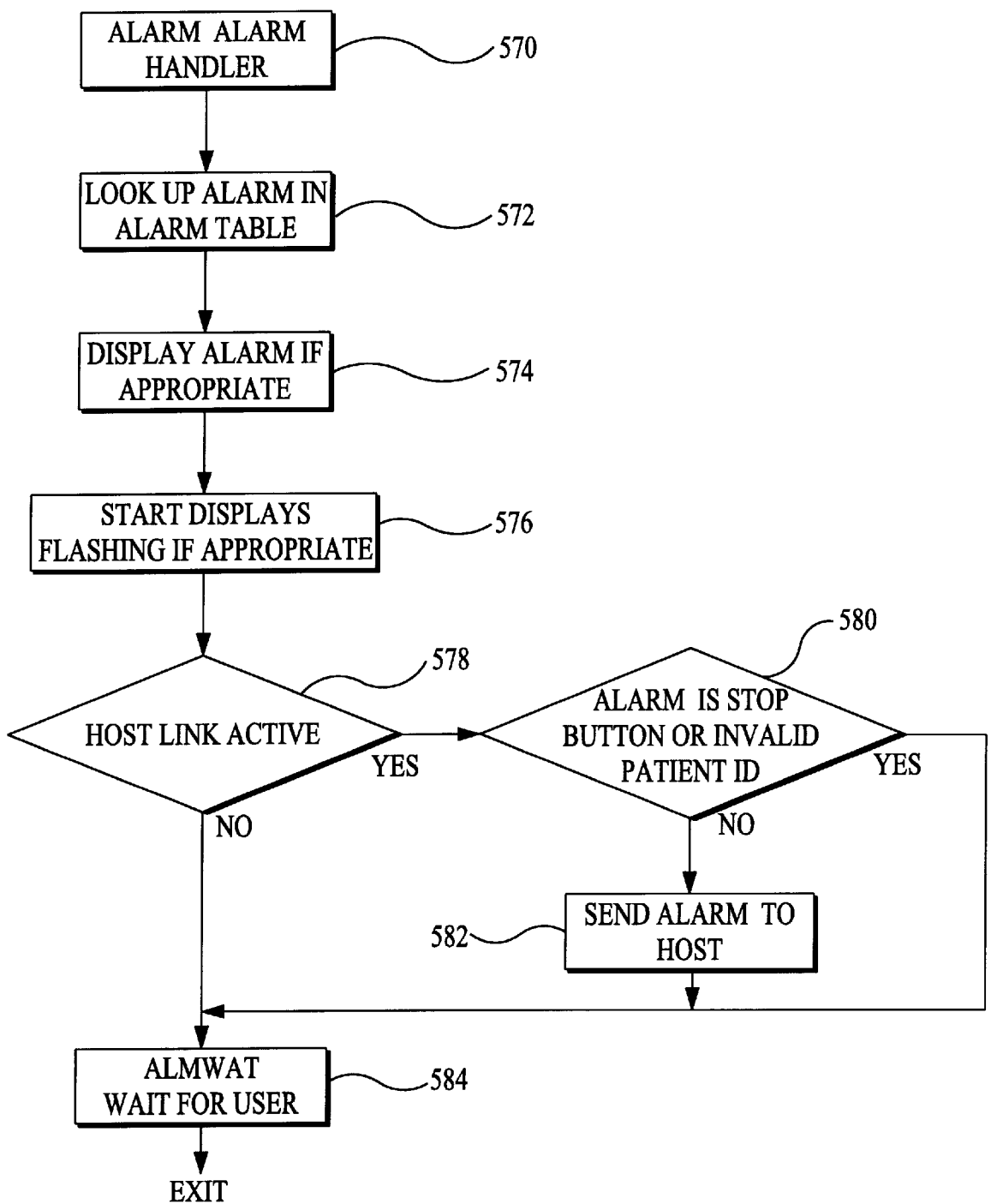

The alarm processing logic is determined by routines that are illustrated in FIGS. 26, 27A, 27B, 28A and 28B which are called into operation whenever an alarm condition exists. As previously described with respect to the flow charts embodying the present invention, there are many different kinds of alarms that can be generated, each of which may result in a different type of alarm condition, such as various displays, including flashing displays and various audio alarms. The software shown in the flowchart of FIG. 26 is initially called with alarm handler block 570 representing the start operation. This results in the software looking up the alarm in an alarm table (block 572) which may result in a display alarm (block 574) or a flashing display (block 576). The subroutine determines whether the host link is active (block 578) which is the link to the control computer that performs various calculations to determine how a prescription is to be compounded, performs the printing of prescription labels and other functions. If the host link is active, the subroutine looks to determine if the alarm condition is one which requires pushing of a stop button to be cleared or if it is an invalid PID (block 580). If either of those occur, then the routine waits for the user to clear the alarm (block 584). If the alarm is not one that results from an invalid PID or requires a stop button to be pressed, the alarm condition is sent to the host computer (block 582) resulting in the same wait state (block 584). In the alarm wait state, the user must either press the STOP button or remove a completed bag in order to clear the alarm.

Figure 27A:
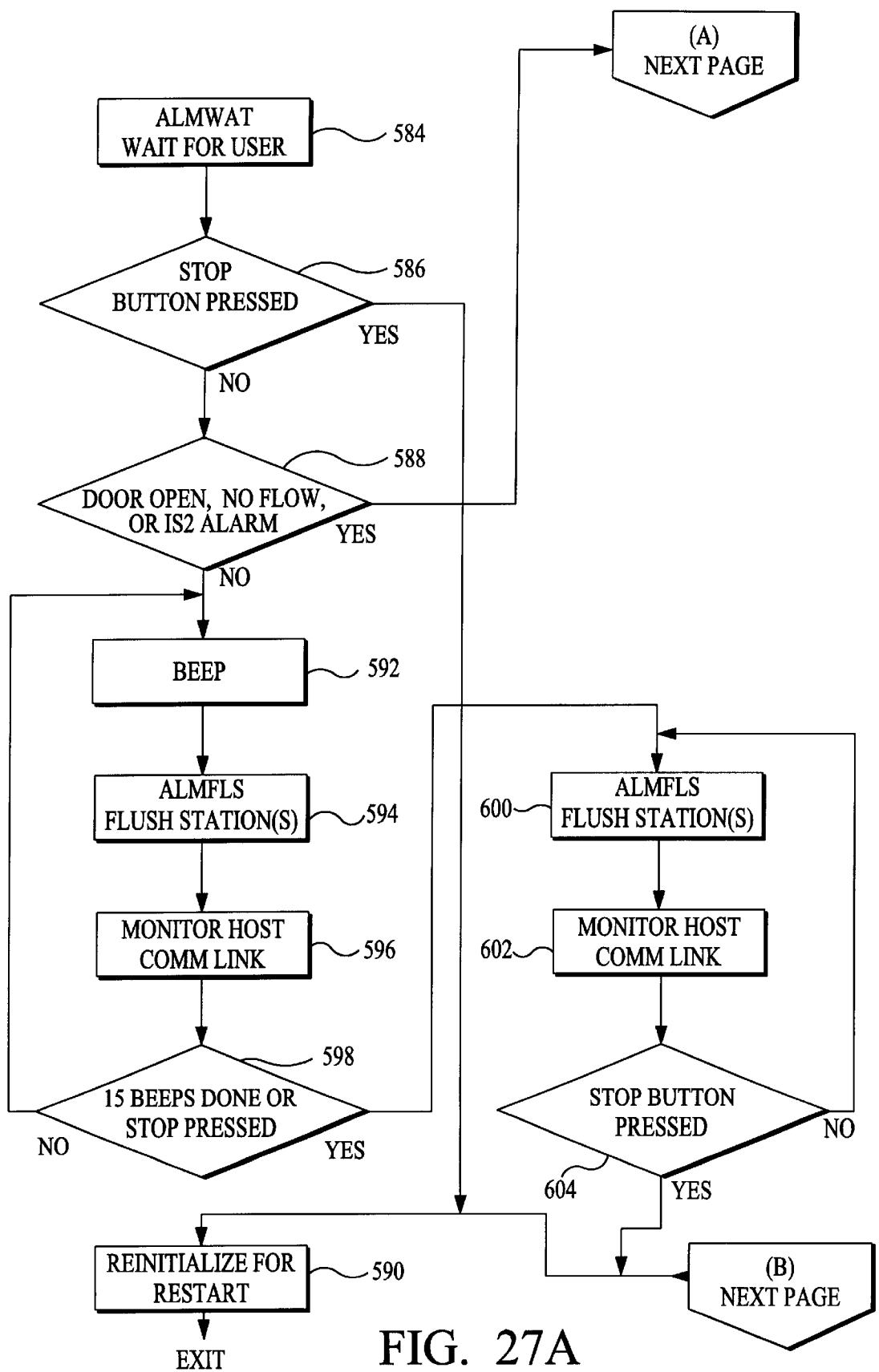
Figure 27B:
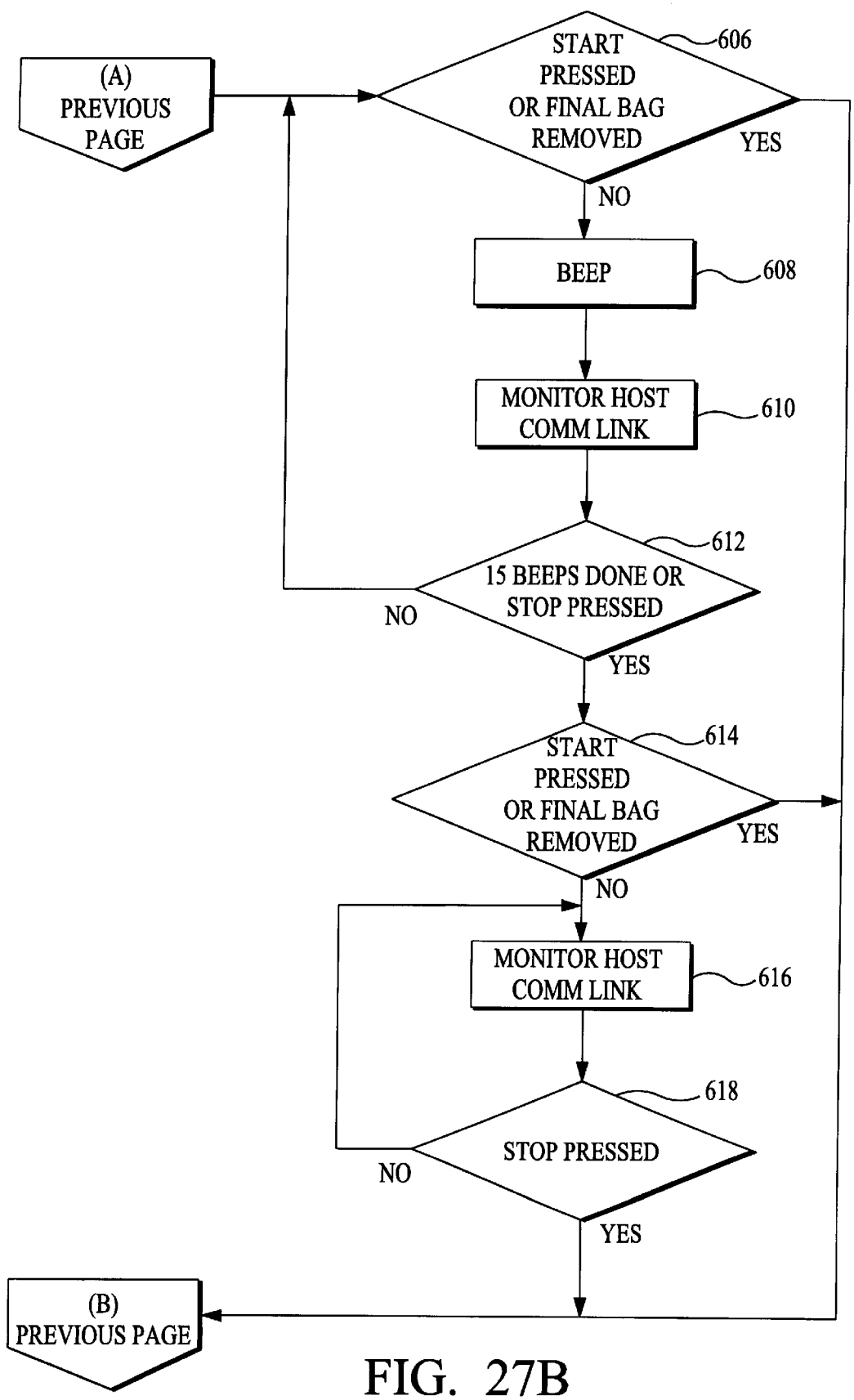

In the subroutine which waits for the user, it is shown in FIGS. 27A and 27B with the initial block 584 beginning the subroutine. The logic determines if the STOP button has been pressed (block 586), which if not results in a determination whether one of the conditions of the door being open, a no flow condition or an incorrect solution 2 alarm having occurred. If the STOP button has been pressed, then the logic reinitializes the system for restart and exits (block 590). It should also be appreciated that in the reinitializing for restart (block 590) does not necessarily enable the user to restart. This is because the decision to permit a restart is one which is determined in the routine that initially cause the alarm routine to be called. If there is not a no flow condition, an incorrect solution 2 alarm or the door open, the subroutine creates a beep signal (block 592) and initiates a flush station subroutine (block 594) and monitors the host communication link (block 596) for determining whether 15 beeps have occurred or a stop button has been pressed (block 598). The significance of the 15 beeps being made is merely to stop beeping after a reasonable time period which is approximately 15 seconds in the preferred embodiment. If either of these have happened, the flush station subroutine is started (block 600), but if not, the subroutine returns to the deep (block 592). If the flush station's subroutine is run (block 600), then the monitor host communication link is then continued to be monitored (block 602) and a determination whether the STOP button has been pressed is made (block 604). If it has been pressed, the system is reinitialized before restart (block 590) but if not, the subroutine returns to flush additional stations. In this regard, it should be recognized that for certain kinds of alarm states, they can be distinguished only by performing a flush operation which is carried out by a user pressing a flush button. It should also be understood that the flush station's subroutine which is shown in FIGS. 28A and 28B does not actually result in stations being flushed, but merely monitors to determine if the flush station buttons have been pressed which then may extinguish the alarm condition.

A positive indication from block 588 causes the routine to move to FIG. 27B and a determination is made as to whether a START button has been pressed or a final bag removed (block 606). If it has been removed, the system is initialized for restart (block 590). If it has not, then a beep is generated (block 608) and the host communication link is monitored (block 610). A determination is then made whether 15 beeps have occurred or the STOP button pressed (block 612) which if not, returns the subroutine to block 606. However, if either of these events have occurred, the subroutine determines if the START button has been pressed or the final bag removed (block 614) which if yes, results in reinitializing for restart (block 590). If not, the subroutine causes the host communication link to be monitored (block 616) until a STOP button has been pressed (block 618). Once the STOP button has been pressed, the system is reinitialized for restart. The need to monitor the host communication link throughout the routine is due to the fact that there are messages that are generated by the host computer that are sent to the compounder, which require an acknowledgement or the host computer will generate an error condition.

Figure 28A:
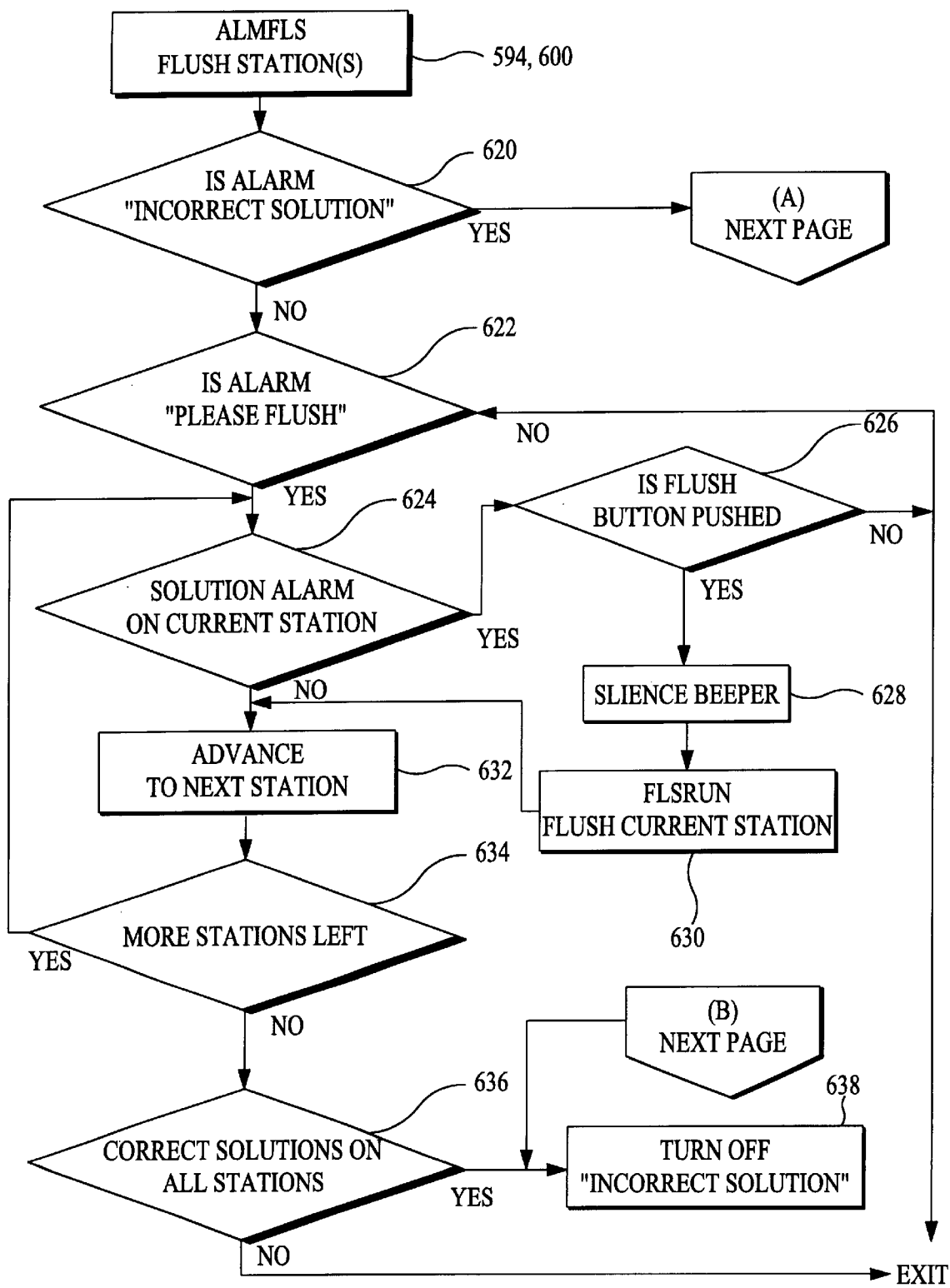
Figure 28B:
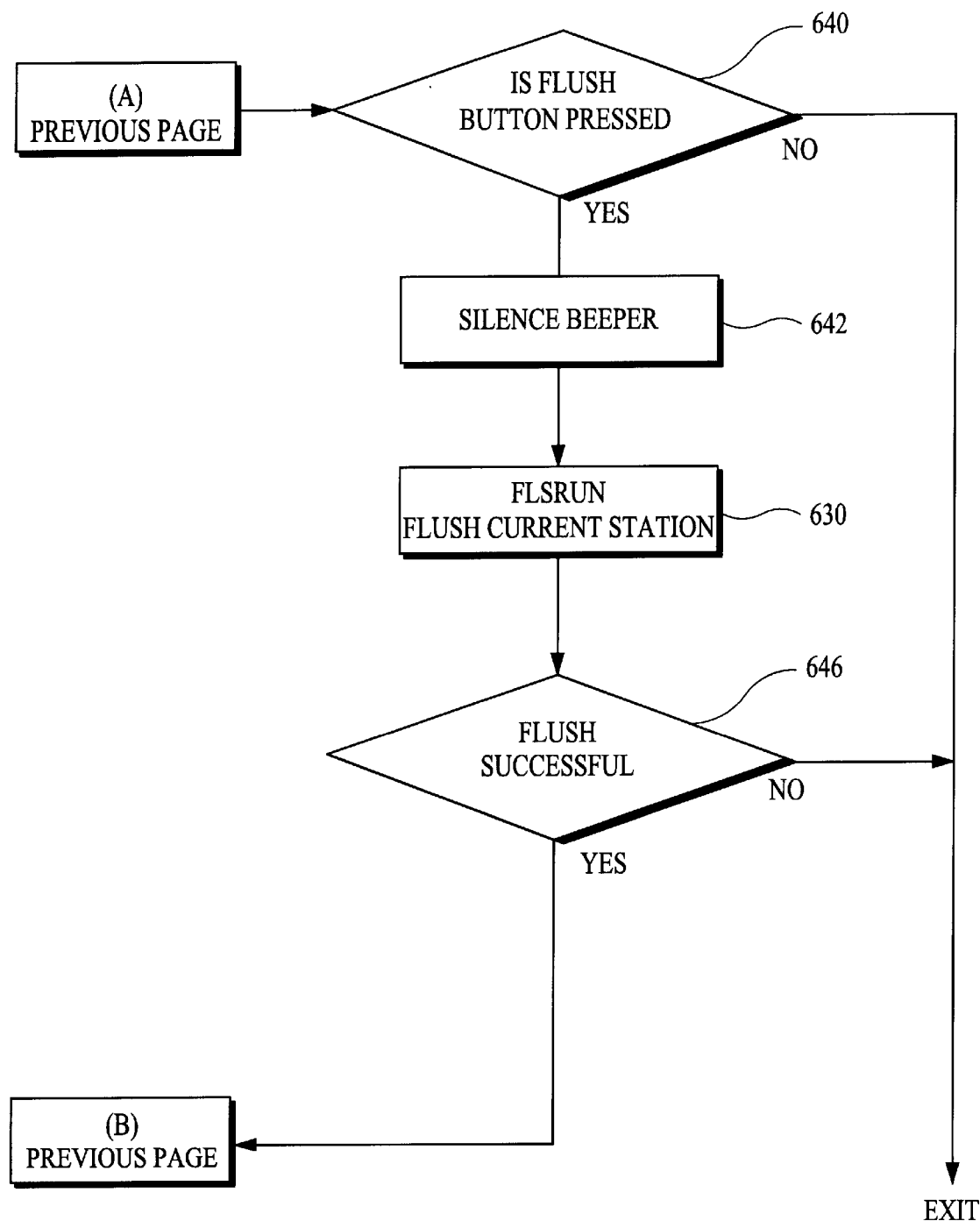

With regard to the alarm flush subroutine and referring to FIGS. 28A and 28B, the subroutine first determines whether the alarm is an incorrect solution alarm (block 620) which if not, results in an inquiry as to whether the alarm is a please flush alarm (block 622). If not, the subroutine is exited, but if yes, the subroutine determines whether if the solution alarm is on a current station (block 624). If it is, the subroutine determines if the flush button has been pressed (block 626), which if not, results in exiting of the subroutine. If it has been pressed, it silences the beeper (block 628) and monitors whether the flush current current station operation has occurred (block 630) and advances to the next station (block 632). If the solution alarm was not on the current station from block 624, the subroutine also causes an advance to the next station (block 632) and thereafter the subroutine determines if there are more stations left (block 634). If there are, it returns to block 624 and if not, an inquiry is made whether there is a correct solution on all stations (block 636). If not, the subroutine is exited. If yes, the incorrect solution alarm indication is turned off (block 638) and the subroutine exited. If the alarm is an incorrect solution alarm from block 620, the subroutine moves to FIG. 28B where a determination is made whether the flush button has been pressed (block 640) which if yes, results in the beeper being silenced (block 642) a flush current station monitoring operation (block 644) occurring and an inquiry as to whether the flush was successful (block 646). If not, the routine is exited, as is the case if the flush button has not detected that it been pressed (block 640). If the flush is successful (block 646), the correct solution indication is turned off (block 638) and the subroutine exited.

Referring to FIG. 1, a further important feature of the present invention is the monitoring of the flushing of the transfer set 14 during such flushing. Previously, to insure that an incorrect solution was entirely removed from the transfer set 14, one had to utilize proxies of a complete flushing of a tube 44 in a transfer set. For example, to insure the required amount of fluid flowed through the transfer tube 44, the weight change in the final container 18 may be monitored. When the necessary weight change occurred which corresponded to a desired flushing amount was registered, the flushing stopped. Alternately, a certain amount of pumping time or number of pumping cycles may have been required when a flushing cycle was initiated. Either way such proxies will likely result in more correct solution being flushed than is necessary which is wasteful.

With the present invention the flushing cycle continues until the proper source solution is registered by the sensing assembly 200. Further, it may be desired that a small additional volume is pumped to compensate for the tubing length between the sensing assembly 200 and manifold 106. Although it may be necessary to utilize other methods to insure the small additional volume is pumped, such volume is small and any waste is likely to be minute.

While various embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

What is claimed is:

1. An assembly for controllably transferring fluids from a plurality of individual source containers through a transfer set of the type which has a plurality of conduits through which fluid can pass to form a desired mixture in a receiving container, each conduit of the set being adapted to place one of the source containers in fluid communication with the receiving container, the assembly comprising:

a pump assembly being adapted to operatively act on fluid in at least one conduit to force a flow of said fluid therethrough, the rate of the flow varying in at least partial dependence on a characteristic of said fluid, said pump assembly operating responsive to predetermined signals being applied thereto;

a first sensor adapted to be in operative contact with the receiving container adapted to generate a signal that is indicative of the weight of the receiving container and its contents;

a second sensor being adapted to be positioned in close proximity to said at least one conduit when properly installed, said second sensor being in noninvasive sensory contact with fluid present in said at least one conduit, and adapted to sense and selectively determine the absence of said at least one conduit, the absence of fluid in said at least one properly installed conduit, and a characteristic of the fluid present in said at least one conduit and generate signals that are indicative of such determination;

a controller for controlling the operation of said apparatus, including said pump assembly and for processing said signals from said first and second sensor and being adapted to generate preselected alarm signals in response to predetermined conditions; and, an alarm indicator operatively connected to said controller for providing preselected alarm indications in response to preselected alarm signals being generated by said controller.

2. An assembly as defined in claim 1 wherein said controller generates one of said preselected alarm signals in response to said second sensor sensing the absence of said conduit.

3. An assembly as defined in claim 2 wherein said alarm indicator includes a display operatively connected to said controller for providing a visual display of said preselected alarms.

4. An assembly as defined in claim 2 wherein said alarm means includes an audible alarm operatively connected to said controller for providing an audible indication of said preselected alarms.

5. An assembly as defined in claim 1 wherein said first sensor includes an extension on which the receiving container is adapted to be removably connected, said controller generating one of said preselected alarm signals in the event said first sensor senses an increase in the weight of the receiving container subsequent to said controller terminating operation of said pump assembly.

6. An assembly as defined in claim 1 wherein said alarm indicator is adapted to provide a no flow alarm indication responsive to said controller generating a no flow alarm signal, and an incorrect solution alarm indication responsive to said controller generating an incorrect solution alarm signal, said controller processing said weight signals and said fluid characteristic signals during operation of said pump assembly and initially generating a no flow alarm signal when said weight signals indicate a less than expected weight change and said fluid characteristic signals are sufficient to generate an incorrect solution alarm signal.

7. An assembly as defined in claim 6 wherein said controller is operative to delay a predetermined time period before said weight signals are processed after initiating operation of said pump assembly.

8. An assembly as defined in claim 1 wherein said pump assembly comprises at least two pumps, each having a pump motor for driving the same, said controller being adapted to control the operation of each pump motor by selectively controlling a main power switch and a pump motor select switch, both of which must be in an operating state to operate a pump motor, said switches being actuated responsive to said controller selectively generating signals for placing said switches in said operating state, said controller placing said main power switch and said pump motor select switch in a nonoperating state in response to said preselected alarm signals being generated.

9. An assembly as defined in claim 8 wherein said controller is adapted to be placed in an idle mode wherein all of said pump motors are not operating and a user of the assembly can input operating and information data into the assembly, said controller placing said main power switch and said pump motor select switch in a nonoperating state in response to said controller being in said idle condition.

10. An assembly as defined in claim 1 wherein said controller is adapted to determine the flow rate of fluid into the receiving container by determining the change in weight of the receiving container per unit of time during operation of said pump assembly.

11. An assembly for controllably transferring fluids from a plurality of individual source containers through a transfer set of the type which has a plurality of conduits through which fluid can pass to form a desired mixture in a receiving container, each conduit of the set being adapted to place one of the source containers in fluid communication with the receiving container, the assembly comprising:

a pump assembly being adapted to operatively act on fluid in at least one conduit to force a flow of said fluid therethrough, the rate of the flow varying in at least partial dependence on a characteristic of said fluid, said pump assembly operating responsive to predetermined signals being applied thereto;

a first sensor adapted to be in operative contact with the receiving container adapted to generate a signal that is indicative of the weight of the receiving container and its contents;

a second sensor being adapted to be positioned in close proximity to said at least one conduit when properly installed, said second sensor being in noninvasive sensory contact with fluid present in said at least one conduit, and adapted to sense and selectively determine a characteristic at least partially identifying the fluid present in said at least one conduit and generate signals that are indicative of such determined characteristic and to sense and selectively determine the absence of fluid in said at least one properly installed conduit and generate signals that are indicative of an empty conduit;

a controller for controlling the operation of said apparatus, including said pump assembly and for processing said signals from said first and second sensor and being adapted to generate preselected alarm signals in response to predetermined conditions, said controller including a memory having data that identifies at least one fluid in said at least one conduit; and, an alarm indicator operatively connected to said controller for providing preselected alarm indications in response to preselected alarm signals being generated by said controller, said alarm indicator being adapted to provide a no flow alarm indication responsive to said controller generating a no flow alarm signal and an incorrect solution alarm indication responsive to said controller generating an incorrect solution alarm signal;

said controller being adapted to begin acquiring a predetermined plurality of said fluid characteristic signals during operation of said pump assembly and compare each of said plurality with said fluid identifying data in said memory and generate an incorrect solution alarm signal when said comparison indicates an incorrect solution;

said controller being adapted to immediately begin acquiring another plurality of characteristic signals in response to said second sensor selectively determining the absence of fluid in said at least one properly installed conduit, thereby precluding completion of said comparison of said earlier acquired characteristic signals and possible generation of an incorrect solution alarm signal.

12. An assembly as defined in claim 11 wherein said plurality comprises 10 successive signals, and said controller generates an incorrect solution signal when 10 successive signals do not correctly compare.

13. An assembly as defined in claim 11 wherein said controller is adapted to generate a no flow alarm signal when a plurality of said weight signals over successive approximately ½ second intervals indicate a less than expected weight change and preclude the generation of an incorrect solution alarm signal.

14. An assembly as defined in claim 11 wherein said pump assembly is adapted to selectively operate at a high speed and a low speed, said controller being precluded from immediately beginning the acquisition of another plurality of characteristic signals in response to said second sensor selectively determining the absence of fluid in said at least one properly installed conduit when said pump assembly is operating at said low speed.

15. An assembly as defined in claim 14 wherein during high speed operation of said pump assembly, said controller delays the acquiring of a predetermined plurality of said fluid characteristic signals during operation of said pump assembly until a predetermined quantity of fluid has been pumped after starting operation of said pump assembly.

16. An assembly for controllably transferring fluids from a plurality of individual source containers through a transfer set of the type which has a plurality of conduits through which fluid can pass to form a desired mixture in a receiving container, each conduit of the set being adapted to place one of the source containers in fluid communication with the receiving container, the assembly comprising:

a pump assembly being adapted to operatively act on fluid in at least one conduit to force a flow of said fluid therethrough, the rate of the flow varying in at least partial dependence on a characteristic of said fluid, said pump assembly operating responsive to predetermined signals being applied thereto;

a first sensor adapted to be in operative contact with the receiving container adapted to generate a signal that is indicative of the weight of the receiving container and its contents;

a second sensor being adapted to be positioned in close proximity to said at least one conduit when properly installed, said second sensor being in noninvasive sensory contact with fluid present in said at least one conduit, and adapted to sense and selectively determine a characteristic at least partially identifying the fluid present in said at least one conduit and generate signals that are indicative of such determined characteristic and to sense and selectively determine the absence of fluid in said at least one properly installed conduit and generate signals that are indicative of an empty conduit;

a controller for controlling the operation of said apparatus, including said pump assembly and for processing said signals from said first and second sensor and being adapted to generate preselected alarm signals in response to predetermined conditions, said controller including memory having data that specifies the weight and identity of fluid in said conduit; and, an alarm indicator operatively connected to said controller for providing preselected alarm indications in response to preselected alarm signals being generated by said controller, said alarm indicator being adapted to provide a no flow alarm indication responsive to said controller generating a no flow alarm signal and an incorrect solution alarm indication responsive to said controller generating an incorrect solution alarm signal;

said controller being adapted to begin acquiring a predetermined plurality of said fluid characteristic signals during operation of said pump assembly and compare each of said plurality with fluid identifying data in said memory and generate an incorrect solution alarm signal when said comparison indicates an incorrect solution;

said controller being adapted to preclude generation of said incorrect solution alarm signal if said weight signal indicates the weight of said receiving container and its contents is within a predetermined amount of said weight of fluids in the receiving container that is indicated by said data in said memory, and the last sensed characteristic corresponded to the identity of the fluid in said at least one conduit that was specified for said conduit in said memory.

17. An assembly for controllably transferring fluids from a plurality of individual source containers through a transfer set of the type which has a plurality of conduits through which fluid can pass to form a desired mixture in a receiving container, each conduit of the set being adapted to place one of the source containers in fluid communication with the receiving container, the assembly comprising:

a pump assembly being adapted to operatively act on fluid in at least one conduit to force a flow of said fluid therethrough, the rate of the flow varying in at least partial dependence on a characteristic of said fluid, said pump assembly operating responsive to predetermined signals being applied thereto;

a first sensor adapted to be in operative contact with the receiving container adapted to generate a signal that is indicative of the weight of the receiving container and its contents;

a second sensor being adapted to be positioned in close proximity to said at least one conduit when properly installed, said second sensor being in noninvasive sensory contact with fluid present in said at least one conduit, and adapted to sense and selectively determine a characteristic at least partially identifying the fluid present in said at least one conduit and generate signals that are indicative of such determined characteristic and to sense and selectively determine the absence of fluid in said at least one properly installed conduit and generate signals that are indicative of an empty conduit;

a controller for controlling the operation of said apparatus, including said pump assembly and for processing said signals from said first and second sensor and being adapted to generate preselected alarm signals in response to predetermined conditions, said controller including memory having data that specifies the weight and identity of fluid in said conduit; and, an alarm indicator operatively connected to said controller for providing preselected alarm indications in response to preselected alarm signals being generated by said controller, said alarm indicator being adapted to provide a no flow alarm indication responsive to said controller generating a no flow alarm signal and an incorrect solution alarm indication responsive to said controller generating an incorrect solution alarm signal;

said controller processing said weight signals during operation of said pump assembly and generating a no flow alarm signal when said weight signals indicate a less than expected weight change;

said controller acquiring a predetermined plurality of said fluid characteristic signals during operation of said pump assembly and comparing each of said plurality with fluid identifying data in said memory and being adapted to generate an incorrect solution alarm signal when said comparison indicates an incorrect solution unless precluded from doing so;

said controller being adapted to preclude generation of said incorrect solution alarm signal if said weight signal indicates the weight of fluid within a portion of said conduit that is located between said receiving container and said second sensor is within a predetermined amount of said specified weight of fluids in the receiving container that is indicated by said data in said memory, and the sensed characteristic approximately corresponding to the fluid immediately before the no flow alarm signal was generated indicated that the fluid was a correct solution, and sensed characteristics since said no flow alarm signal was generated indicated that said conduit is empty, said controller then operating said pump assembly to pump said fluid in said portion of said conduit into the receiving container.

18. An assembly for selectively transferring fluids from one or more source containers to form a desired mixture in a receiving container, the assembly comprising:

a pump assembly being adapted to force fluid through each conduit responsive to applied drive signals;

a first sensor assembly for generating a signal that is indicative of the weight of the receiving container;

a second sensor assembly in noninvasive sensory contact with fluid present in a portion of a conduit extending between the source container and the receiving container, the second sensor being adapted to selectively determine the absence of a conduit, the presence of an empty conduit, and a characteristic of the fluid present in the conduit and to generate signals that are indicative of such determinations;

a controller for controlling the pump assembly, for processing the signals from the sensor assemblies, and for selectively generating alarm signals; and, an alarm indicator connected to the controller for providing alarms when alarm signals are received from the controller.

19. An assembly for selectively transferring fluids from one or more source containers to form a desired mixture and goal weight in a receiving container, the assembly comprising:

a pump assembly being adapted to force fluid through each conduit responsive to applied drive signals;

a first sensor assembly for generating a signal that is indicative of the weight of the receiving container and its contents;

a second sensor assembly in noninvasive sensory contact with fluid present in a portion of a conduit extending between the source container and the receiving container, the second sensor being adapted to selectively determine the absence of a conduit, the presence of an empty conduit, and a characteristic of the fluid at least partially identifying the fluid present in the conduit and to generate signals that are indicative of such determinations;

a controller for controlling the pump assembly, for processing the signals from the sensor assemblies, and for selectively generating alarm signals, the controller also including a memory having data that specifies the identity of predetermined fluids that may be in the conduit; and, an alarm indicator connected to the controller for providing preselected alarms when preselected alarm signals are received from the controller, the alarm indicator being adapted to provide a no flow alarm indication when a no flow alarm signal is received from the controller and an incorrect solution alarm indication when an incorrect solution alarm signal is received from controller;

the controller acquiring a number of fluid characteristic signals during operation of the pump assembly and comparing each of them with fluid identifying data in the memory and generating an incorrect solution alarm signal when the comparison indicates an incorrect solution, unless the weight signal indicates the weight of the receiving container is within a small amount of the goal weight, and the last sensed characteristic corresponded to the identity of the fluid in the conduit that was specified for the conduit.

20. An assembly for selectively transferring fluids from one or more source containers through respective conduits to form a desired mixture in a receiving container having a goal weight, the assembly comprising:

a pump assembly being adapted to force fluid through each conduit responsive to applied drive signals;

a first sensor assembly for generating a signal that is indicative of the weight of the receiving container and its contents;

a second sensor assembly in noninvasive sensory contact with fluid present in a portion of a conduit extending between the source container and the receiving container, the second sensor being adapted to selectively determine the absence of a conduit, the presence of an empty conduit, and a characteristic of the fluid at least partially identifying the fluid present in the conduit and to generate signals that are indicative of such determinations;

a controller for controlling the pump assembly, for processing the signals from the sensor assemblies, and for selectively generating alarm signals, the controller also including a memory having data that specifies the identity of predetermined fluids that may be in the conduit; and, an alarm indicator connected to the controller for providing preselected alarms when preselected alarm signals are received from the controller, the alarm indicator being adapted to provide a no flow alarm indication when a no flow alarm signal is received from the controller and an incorrect solution alarm indication when an incorrect solution alarm signal is received from controller;

the controller acquiring a number of fluid characteristic signals during operation of the pump assembly and comparing each of them with fluid identifying data in the memory and generating an incorrect solution alarm signal when the comparison indicates an incorrect solution, unless the weight signal indicates the weight of fluid within a portion of the conduit that is located between the receiving container and the second sensor is within a predetermined amount of said specified weight of fluids in the receiving container that is indicated by said data in said memory, and the sensed characteristic approximately corresponding to the fluid immediately before the no flow alarm signal was generated indicated that the fluid was a correct solution, and sensed characteristics since said no flow alarm signal was generated indicated that the conduit is empty, the controller then operating the pump assembly to pump the fluid in the portion of the conduit into the receiving container.

21. An assembly for controllably transferring fluids from a plurality of individual source containers through a transfer set of the type which has a plurality of conduits through which fluid can pass to form a desired mixture in a receiving container, each conduit of the set being adapted to place one of the source containers in fluid communication with a manifold junction that is in fluid communication to the receiving container via a manifold transfer conduit, the assembly comprising:

- a pump assembly being adapted to operatively act on fluid in at least one conduit to force a flow of said fluid therethrough, the rate of the flow varying in at least partial dependence on a characteristic of said fluid, said pump assembly operating responsive to predetermined signals being applied thereto;
- a first sensor adapted to be in operative contact with the receiving container adapted to generate a signal that is indicative of the weight of the receiving container and its contents;
- a second sensor being adapted to be positioned in close proximity to said junction transfer conduit or one of said transfer set conduits, said second sensor being in noninvasive sensory contact with fluid present in said conduit, and adapted to sense and selectively determine the absence of said at least one conduit, the absence of fluid in said conduit, and a characteristic of the fluid present in said conduit and generate signals that are indicative of such determination;
- a controller for controlling the operation of said apparatus, including said pump assembly and for processing said signals from said first and second sensor and being adapted to generate preselected alarm signals in response to predetermined conditions; and,
- an alarm indicator operatively connected to said controller for providing preselected alarm indications in response to preselected alarm signals being generated by said controller.

22. An assembly for selectively transferring fluids from one or more source containers to form a desired mixture in a receiving container, the assembly comprising:

- a pump assembly being adapted to force fluid through each conduit responsive to applied drive signals;
- a first sensor assembly for generating a signal that is indicative of the weight of the receiving container;
- a second sensor assembly in noninvasive sensory contact with fluid present in a portion of a conduit extending between the source container and the receiving container, the second sensor being adapted to selectively determine the absence of a conduit, the presence of an empty conduit, and a characteristic of the fluid present in the conduit and to generate signals that are indicative of such determinations;
- a controller for controlling the pump assembly, for processing the signals from the sensor assemblies, and for selectively generating alarm signals; and,
- an alarm indicator connected to the controller for providing alarms when alarm signals are received from the controller;
- said controller monitoring said first sensor assembly signals and data relating to the desired mixture being formed in the receiving container, and determining whether weight gain is occurring after completion of compounding of the desired mixture when said pump assembly is not operating, said controller inhibiting generation of an alarm signal for a predetermined time period after receiving signals from said first sensor assembly indicating a weight gain have been received, said controller receiving signals from said first sensor assembly to determine if the container weight returns to the completed weight that existed before said signals were received indicating a weight gain had occurred, and generating an alarm signal in the event the completed weight is not returned.

23. An assembly as defined in claim 22 wherein said predetermined time period is within the range of about 5 to about 20 seconds.

* * * * *